United States Patent [19]
Lennert et al.

[11] Patent Number: 5,792,944
[45] Date of Patent: Aug. 11, 1998

[54] POWER SUPPLY MONITOR AND CONTROL FOR MEDICAL INSTRUMENT

[75] Inventors: George R. Lennert, Fishers; Rick L. Collins; William J. Murphy, both of Cicero, all of Ind.

[73] Assignee: Boehringer Mannheim Corporation, Indianapolis, Ind.

[21] Appl. No.: 697,019

[22] Filed: Aug. 16, 1996

Related U.S. Application Data

[63] Continuation of Ser. No. 114,914, Aug. 31, 1993, abandoned.

[51] Int. Cl.⁶ .................................................. A61B 5/60
[52] U.S. Cl. ................... 73/64.43; 73/53.001; 307/66; 307/87
[58] Field of Search ............................. 128/637, 658, 128/635; 307/66, 87; 364/750; 73/53.01, 64.43

[56] References Cited

U.S. PATENT DOCUMENTS

| | | |
|---|---|---|
| 3,695,842 | 10/1972 | Mintz . |
| 4,698,530 | 10/1987 | Thomson . |
| 4,713,555 | 12/1987 | Lee . |
| 4,756,884 | 7/1988 | Hillman et al. . |
| 4,849,340 | 7/1989 | Oberhardt . |
| 4,868,832 | 9/1989 | Marrington et al. ............ 364/750 |
| 4,951,171 | 8/1990 | Tran et al. . |
| 4,963,498 | 10/1990 | Hillman et al. . |
| 5,010,469 | 4/1991 | Bobry ............................ 307/66 |
| 5,053,199 | 10/1991 | Keiser et al. . |
| 5,110,727 | 5/1992 | Oberhardt . |
| 5,117,324 | 5/1992 | Johnson, Jr. . |
| 5,138,872 | 8/1992 | Henderson .................... 73/64.41 |
| 5,140,161 | 8/1992 | Hillman et al. . |
| 5,167,145 | 12/1992 | Butler et al. . |
| 5,341,034 | 8/1994 | Matthews ...................... 307/66 |

FOREIGN PATENT DOCUMENTS

| | | |
|---|---|---|
| 0394041 | 10/1990 | European Pat. Off. . |
| WO 92/01065 | 1/1992 | WIPO . |

Primary Examiner—Robert L. Nasser
Attorney, Agent, or Firm—Barnes & Thornburg

[57] ABSTRACT

An instrument for determining a characteristic of a biological fluid or a control comprises a radiation-reflective surface, a first source for irradiating the surface, a first detector for detecting radiation reflected from the surface, and a mechanism for determining the characteristic based on the detected radiation. A slide holds a sample of the biological fluid or control the characteristic of which is to be determined. The slide has two opposed walls transparent to the radiation. The first source and first detector are disposed adjacent a first one of the two opposed walls and the radiation reflective surface is disposed adjacent a second of the two opposed walls. A system is provided for supplying power and regulating supplied power from one of multiple power sources to the instrument. The system comprises first and second power sources, first coupling circuitry for selectively coupling the system to the first power source, second coupling circuitry for selectively coupling the system to the second power source, and circuitry for comparing a voltage supplied by the first power source to a voltage supplied by the second power source and for controlling the first coupling circuitry to decouple the system from the first power source when the voltage supplied by the second power source exceeds the voltage supplied by the first power source.

15 Claims, 17 Drawing Sheets

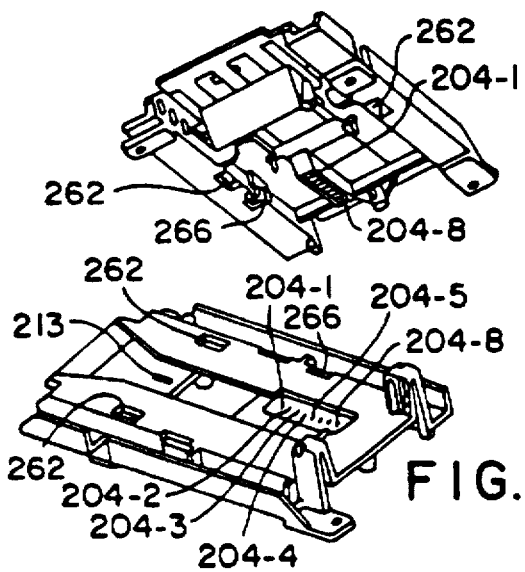
FIG. 8C
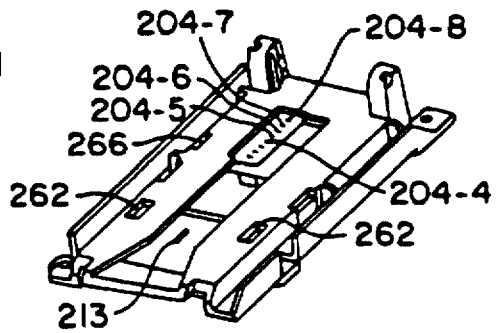
FIG. 8B
FIG. 8A
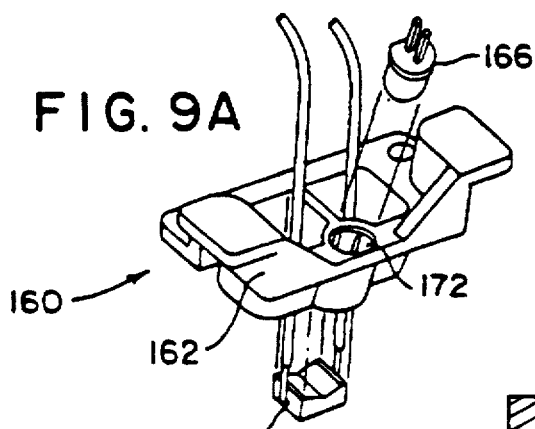
FIG. 9A
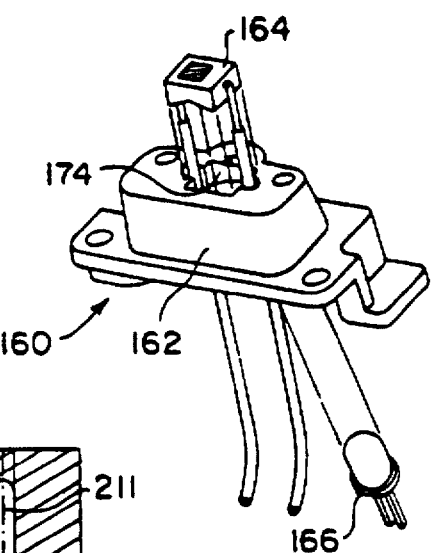
FIG. 9B
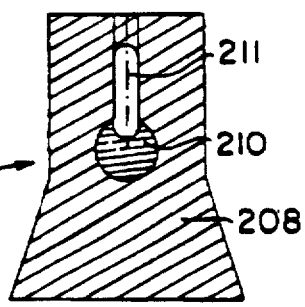
FIG. 10

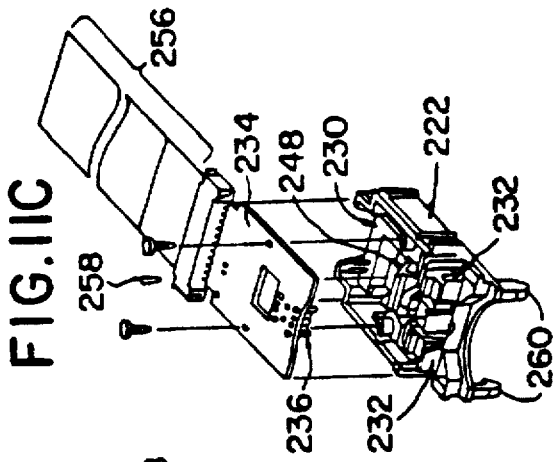
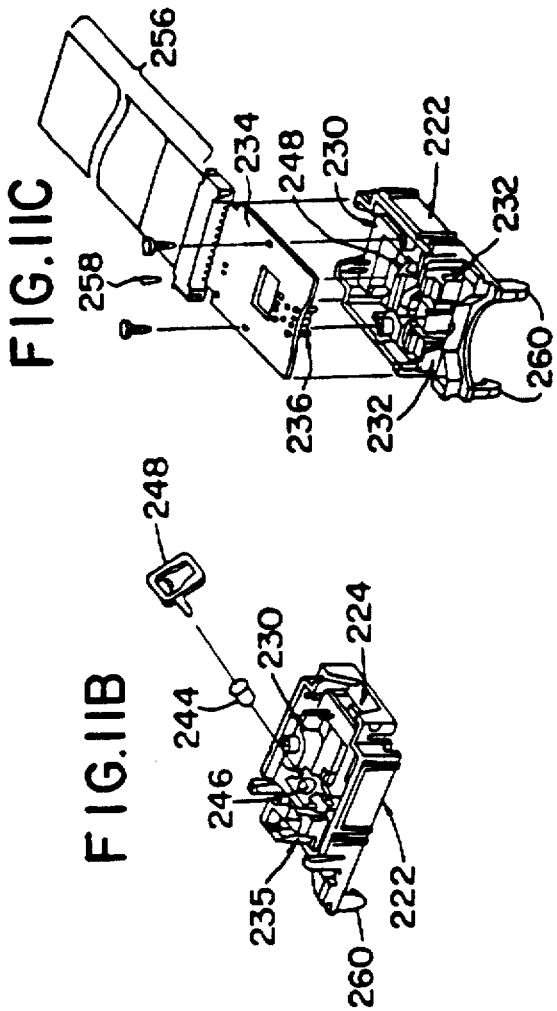
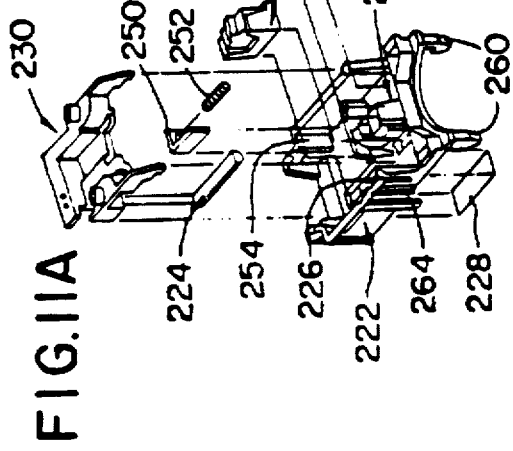
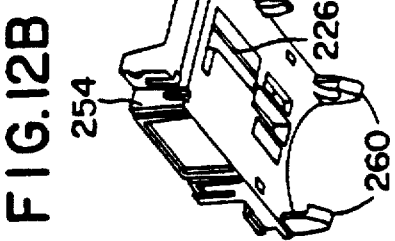
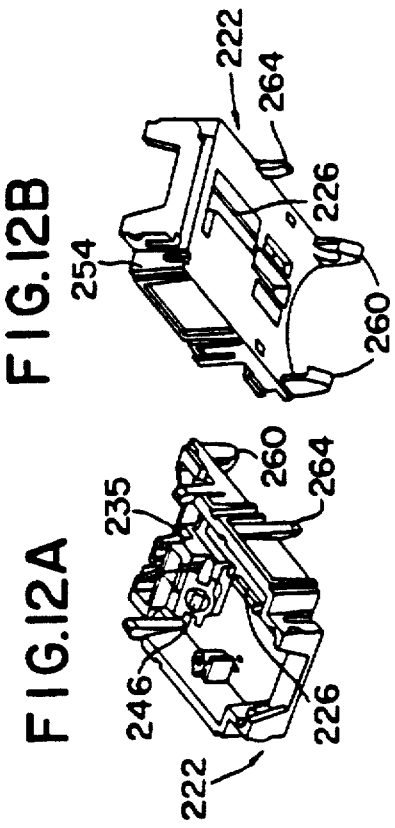
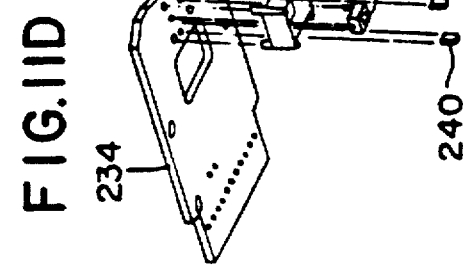

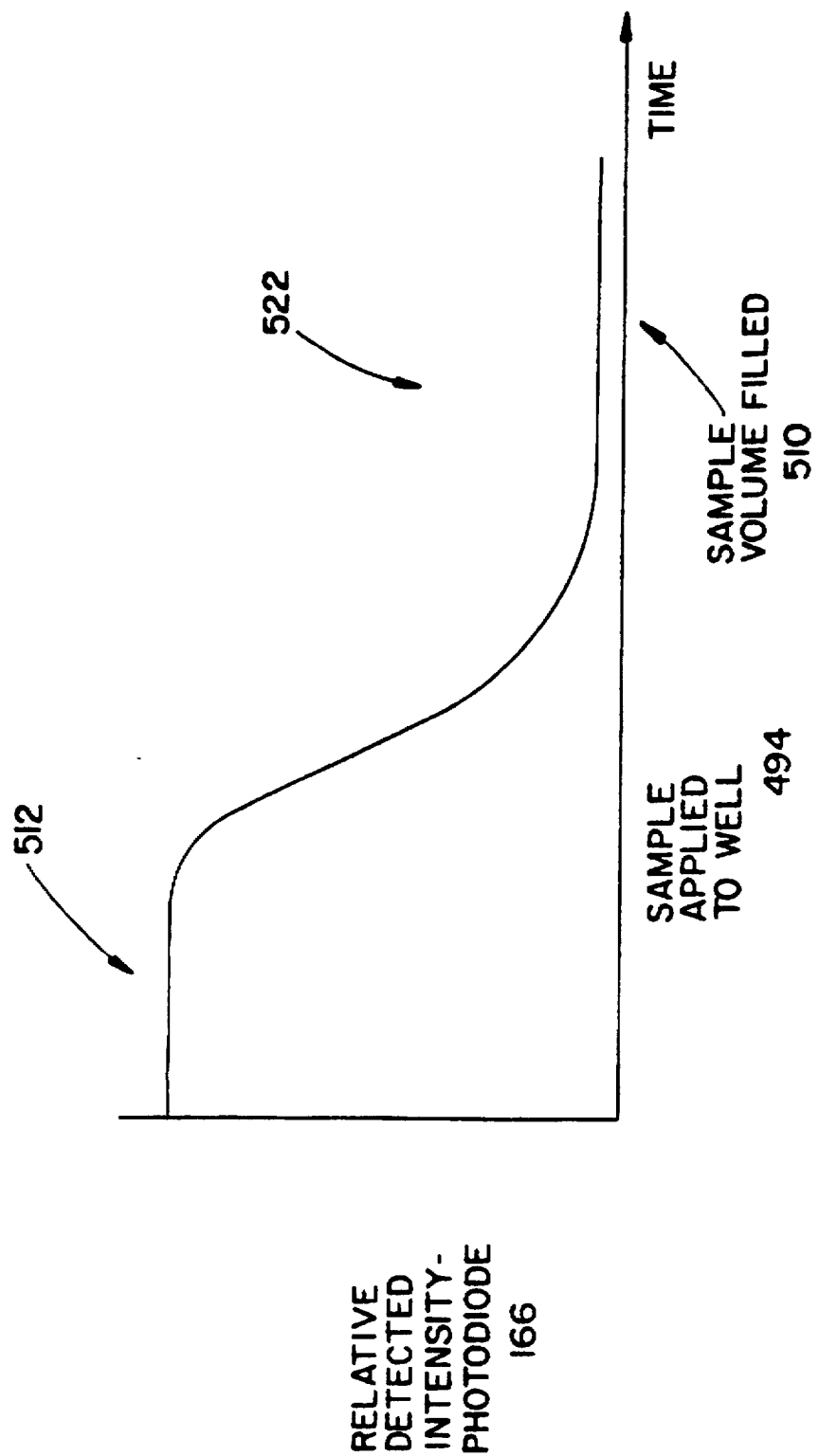

POWER SUPPLY MONITOR AND CONTROL FOR MEDICAL INSTRUMENT

This application is a continuation of application Ser. No. 08/114,914, filed Aug. 31, 1993, now abandoned.

This is also a related application to U.S. Ser. No. 08/114,915, titled ANALOG HEATER CONTROL FOR MEDICAL INSTRUMENT, filed Aug. 31, 1993, now abandoned, U.S. Ser. No. 08/149,113, titled FLUID DOSE, FLOW AND COAGULATION SENSOR FOR MEDICAL INSTRUMENT, filed Aug. 31, 1993, now U.S. Pat. No. 5,522,255, U.S. Ser. No. 08/114,896, titled MAGNETIC SYSTEM FOR MEDICAL INSTRUMENT, filed Aug. 31, 1993, titled REAGENT AND METHOD OF ITS USE, filed Aug. 31, 1993, now abandoned, and U.S. Ser. No. 08/114,897, titled METHOD AND APPARATUS FOR OPERATING A MEDICAL INSTRUMENT, filed Aug. 31, 1993, now U.S. Pat. No. 5,526,111, all filed on the same data as this application and assigned to the same assignee, the disclosure of which is incorporated herein by reference.

This invention relates to methods and apparatus for determining/detecting power supply undervoltage conditions. It is disclosed in the context of digital control circuitry for a blood coagulation instrument but is believed to be useful in other contexts as well.

At present supply voltage supervision in blood coagulation testing instruments and the like comprises monolithic integrated circuits (IC's) specifically designed as reset controllers in microcontroller (μC) or microprocessor (μP) power supply systems. No system is known in the current art which combines isolation of multiple (illustratively, two) power supplies, reverse polarity protection, undervoltage protection, protection against power supply voltage about to go out of limits ("fall-out") protection, and regulation all onto one IC.

According to the invention, a system is provided which can be incorporated into a single IC which monitors a power supply for undervoltage and/or overvoltage conditions.

According to the invention, a system is provided for inexpensively determining/detecting power supply undervoltage conditions. This, in turn, provides a method for orderly shutdown of the system supplied with power by the power supply. It also provides a method for the prevention of turn-on of the system supplied with power by the power supply.

According to the invention, a system is provided for inexpensively detecting power supply, for example, battery, polarity reversal, thereby preventing component and system failures which might otherwise attend such polarity reversal.

According to the invention, a system is provided for inexpensively isolating multiple power supplies, such as a battery and an AC/DC adapter power supply, from each other while minimizing potential drops across the isolating components in line with the multiple power supplies.

According to the invention, a power supply control and voltage supervisory circuit provides orderly turn-on and shutdown of a system powered by the power supply. The control and supervisory circuit provides proper power supply voltage levels and polarities in addition to regulation.

According to the invention multiple system power sources are isolated from each other. The power source with the largest-magnitude potential is monitored. Its status is supplied to a μC to prevent power failure from disrupting the system powered by the power supplies.

A power supply circuit is so designed that the battery power source and the AC/DC adapter power source are isolated from each other through diode and transistor protection. The circuit prevents the AC/DC adapter from charging the battery power source hazardously. The circuit further prevents the battery power source from powering the AC/DC adapter power source front end, thereby extending the life of the battery. In addition, isolation disconnects both power sources from the system electronics when the system is turned off, thereby preventing power loss.

The system is so designed that if both power sources are connected to the system, the power source with the greater potential (ordinarily the AC/DC adapter) overrides the power source(s) with less potential (ordinarily the battery) upon powering up of the system, extending the life of the power source(s) with less potential.

Protection is provided against accidental polarity reversal of either power source. In the case of the battery power source, if any of the batteries is (are) installed backwards, the system will not turn on, even if the AC/DC adapter is connected with the correct polarity.

A voltage monitor circuit performs a "watchdog" function to prevent the unit from turning on and possibly locking up due to low power source voltages. In carrying out this watchdog function, the system only turns on if the primary power source potential is greater than an established limit. The voltage monitor circuit is hardware programmable to vary this voltage. If the power source potential is greater than the established limit, then the μC will latch system power fully on.

Additional power fault protection is provided through an error-output terminal of a five volt regulator in the system. If the system voltage is about to fall out of regulation, the μC is warned of the anticipated fall out. The μC is provided with sufficient advance warning of the fallout to shut down the system in an orderly fashion.

According to an aspect of the invention, a system for supplying power and regulating supplied power from one of multiple power sources comprises first coupling means for selectively coupling the system to a first power source, second coupling means for selectively coupling the system to a second power source, and means for comparing the voltage supplied by the first power source to the voltage supplied by the second power source and for controlling the first coupling means to decouple the system from the first power source when the voltage supplied by the second power source exceeds the voltage supplied by the first power source.

Illustratively, the system is incorporated into an instrument for measuring the clotting time of blood, a blood fraction or a control.

Further, illustratively, the first power source comprises a battery provided in the instrument and the second power source comprises an AC-to-DC converter for supplying a voltage having a higher magnitude than the battery's voltage when the converter is coupled to a line voltage source.

Additionally, illustratively, the instrument comprises an ON/OFF switch for energizing the instrument. Third coupling means selectively couple one of the first and second coupling means to the instrument. The third coupling means is coupled to the ON/OFF switch. Means are provided for coupling the third coupling means to the first and second coupling means.

Further, illustratively, the system comprises a controller for energizing and orderly de-energizing the instrument. Means are provided for storing sufficient energy to permit the controller to orderly de-energize the instrument. Means monitor the voltage supplied to the instrument by one of the first and second power sources and signal the controller to orderly de-energize the instrument if the monitored voltage does not exceed a threshold. Fourth means are provided for coupling the controller to the means for storing sufficient energy to permit the controller to orderly de-energize the instrument. Fifth means couple the means for monitoring the voltage supplied to the instrument by one of the first and second power sources to the first and second coupling means. Sixth means couple the means for monitoring the voltage supplied to the instrument by one of the first and second power sources to the controller.

According to another aspect of the invention, a method for supplying power and regulating supplied power comprises providing first and second power sources, comparing the voltage supplied by the first power source to the voltage supplied by the second power source, providing means for selectively coupling a circuit to be powered selectively by the first power source or the second power source to the first power source, and decoupling the circuit from the first power source when the voltage supplied by the second power source exceeds the voltage supplied by the first power source.

Illustratively, according to this aspect of the invention, the method further comprises incorporating the circuit into an instrument for measuring the clotting time of blood, a blood fraction or a control.

Further, illustratively, the step of providing first and second power sources comprises providing a battery in the instrument and providing an AC-to-DC converter for supplying a voltage having a higher magnitude than the magnitude of the battery's voltage when the converter is coupled to a line voltage source.

Additionally, illustratively, the method comprises providing the instrument with an ON/OFF switch for energizing the instrument, and coupling one of the first and second power sources by the ON/OFF switch to the instrument.

Further, illustratively, the method comprises storing sufficient energy to permit orderly de-energizing of the instrument, monitoring the voltage supplied to the instrument by one of the first and second power sources, signalling an instrument controller to orderly de-energize the instrument if the monitored voltage does not exceed a threshold, and orderly de-energizing the instrument.

The invention may best be understood by referring to the following description and accompanying drawings which illustrate the invention. In the drawings.

Figure 1:
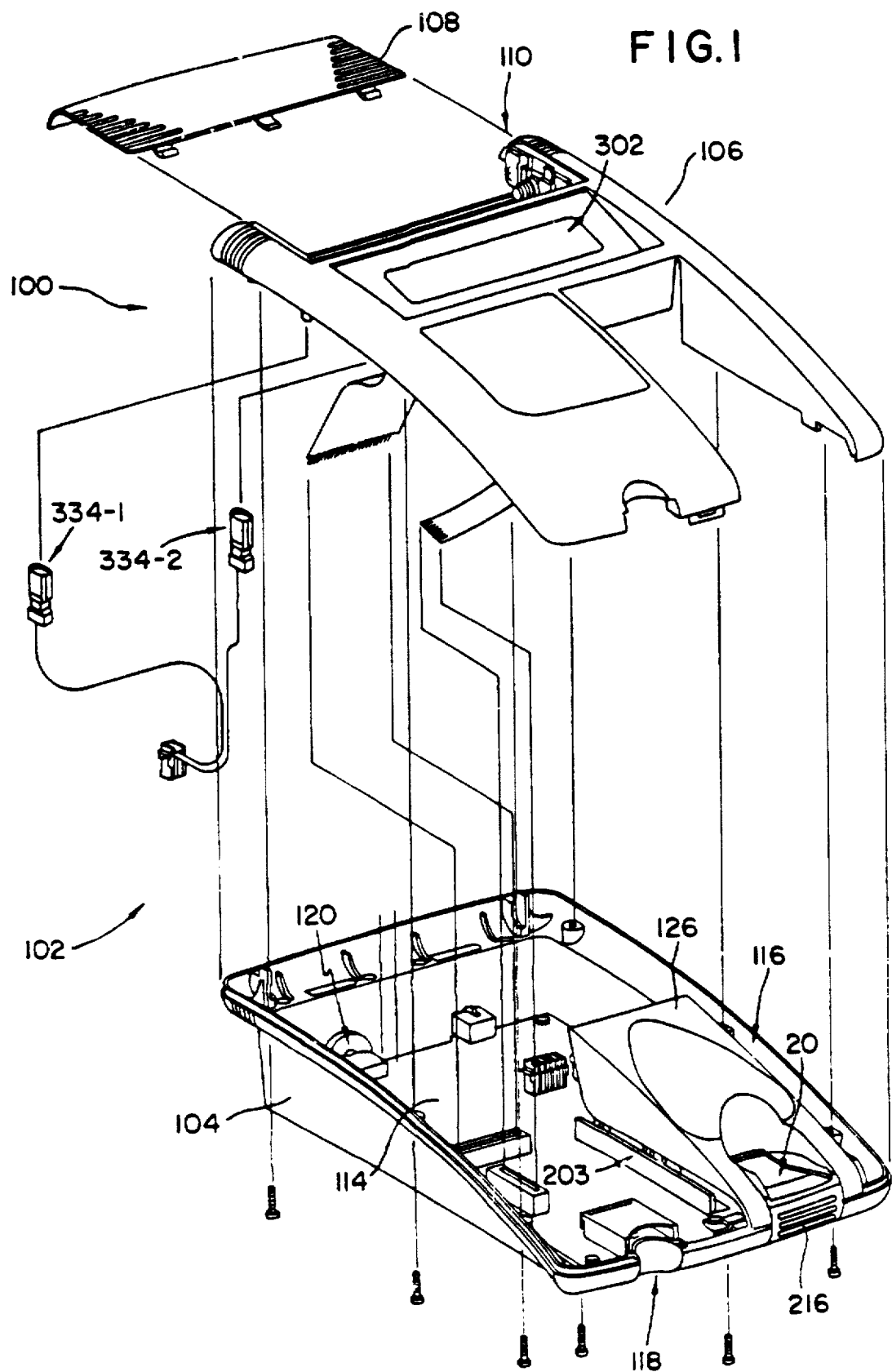
FIG. 1 illustrates an exploded perspective view of an instrument constructed according to the present invention.
Figure 2:
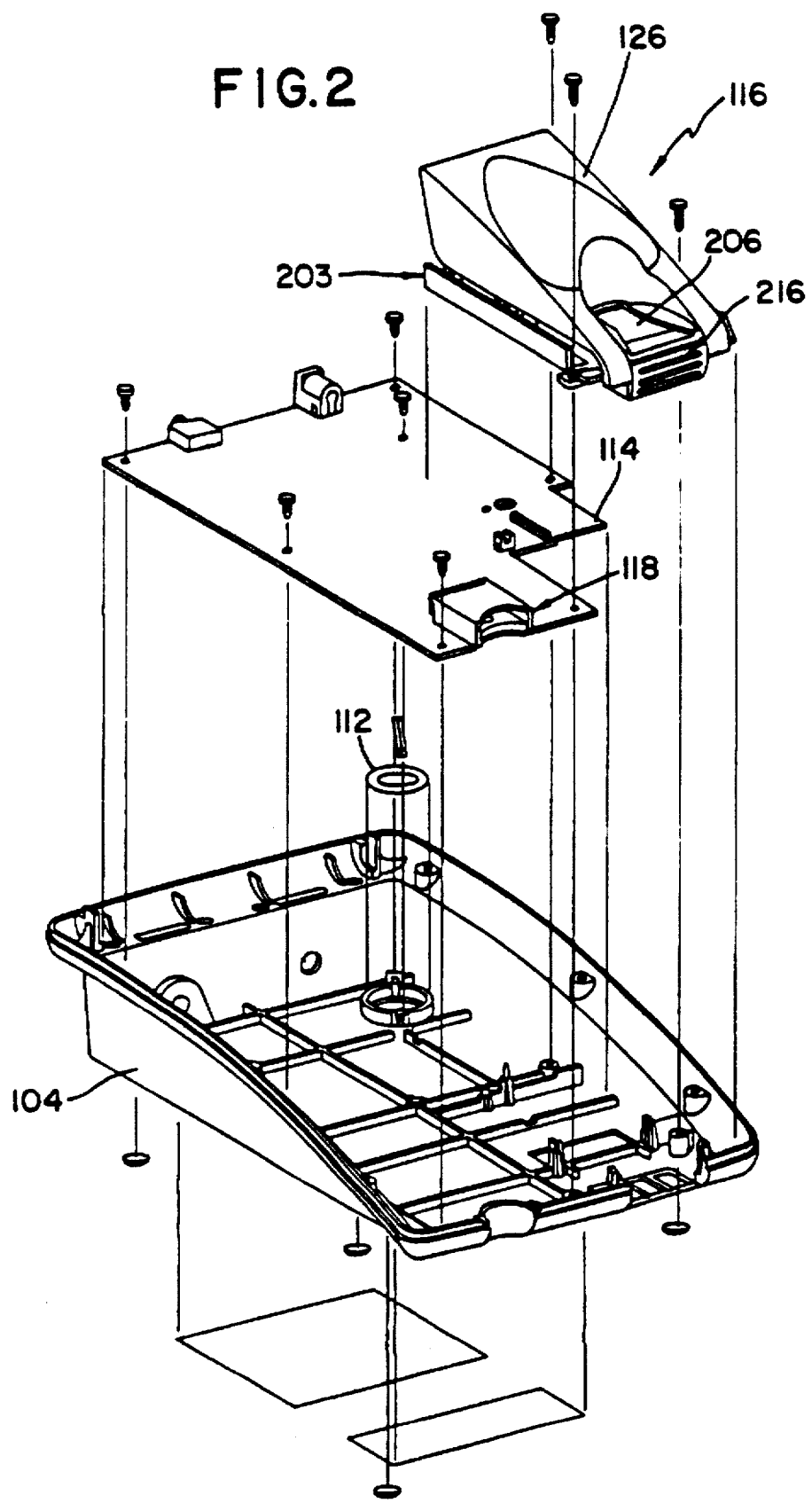
FIG. 2 illustrates a fragmentary exploded perspective view of the bottom portion of the instrument illustrated in FIG. 1.
Figure 3:
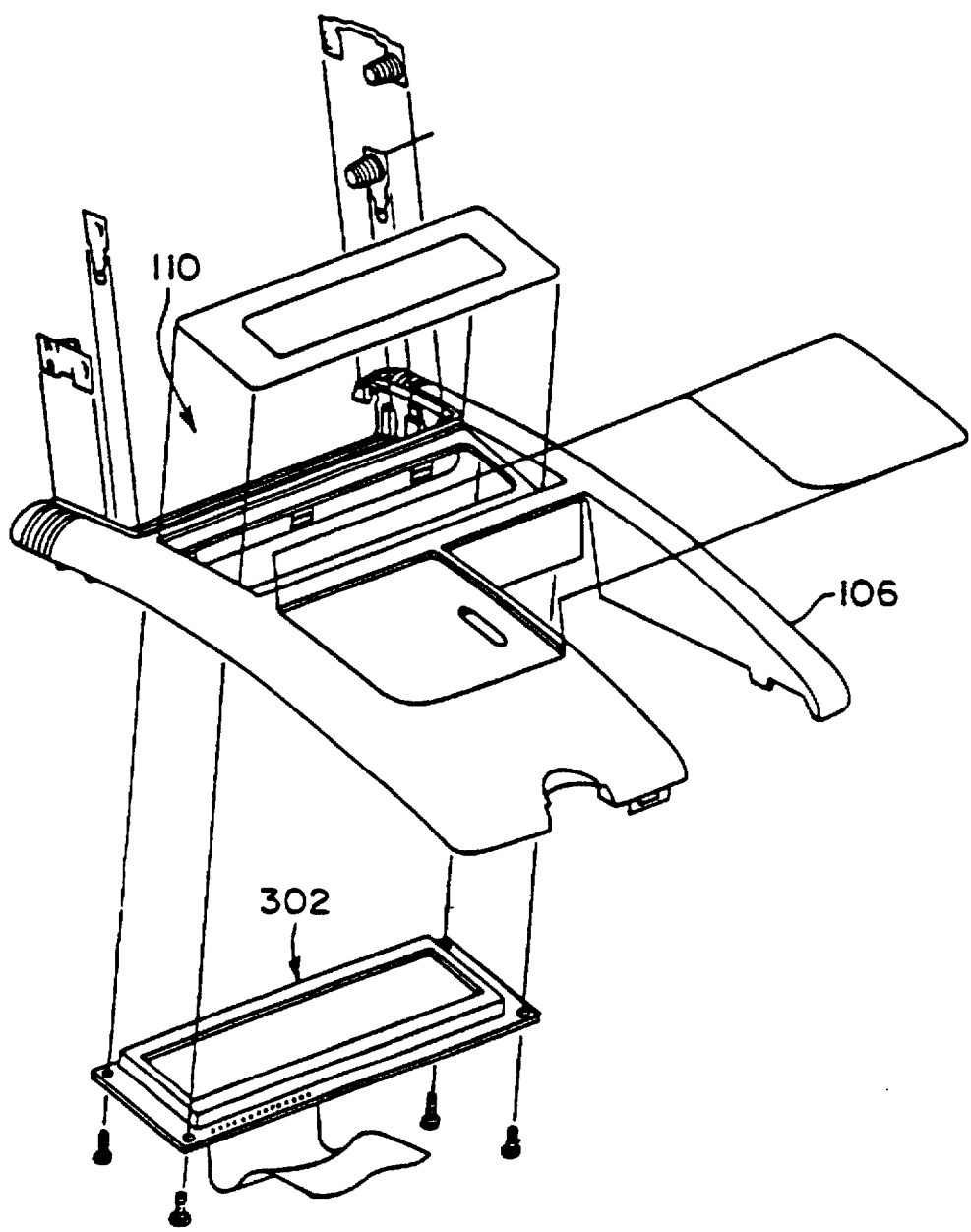
FIG. 3 illustrates a fragmentary exploded perspective view of the top portion of the instrument illustrated in FIG. 1.
Figure 4:
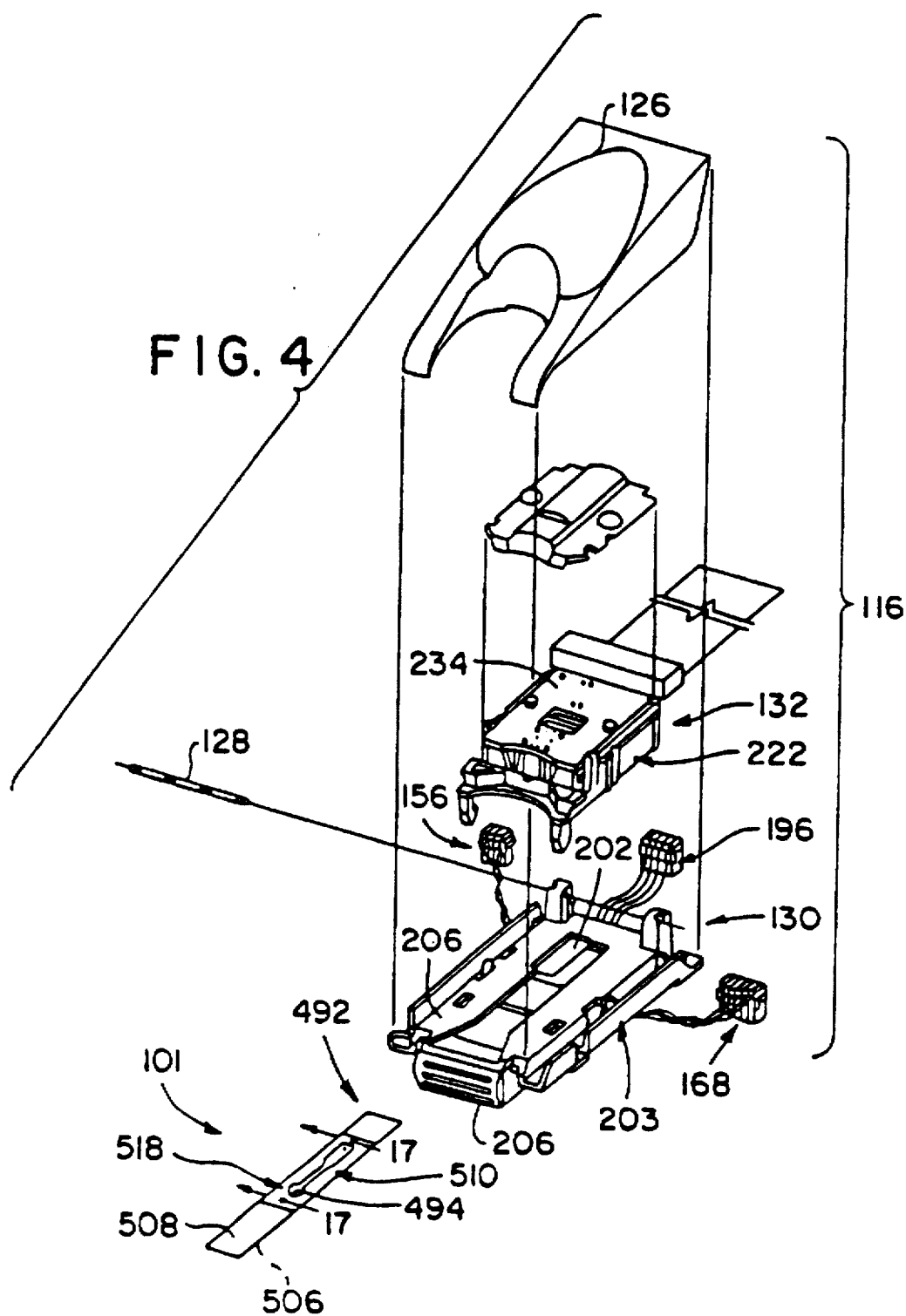
FIG. 4 illustrates an exploded perspective view of a detail of FIG. 1.
Figure 5:
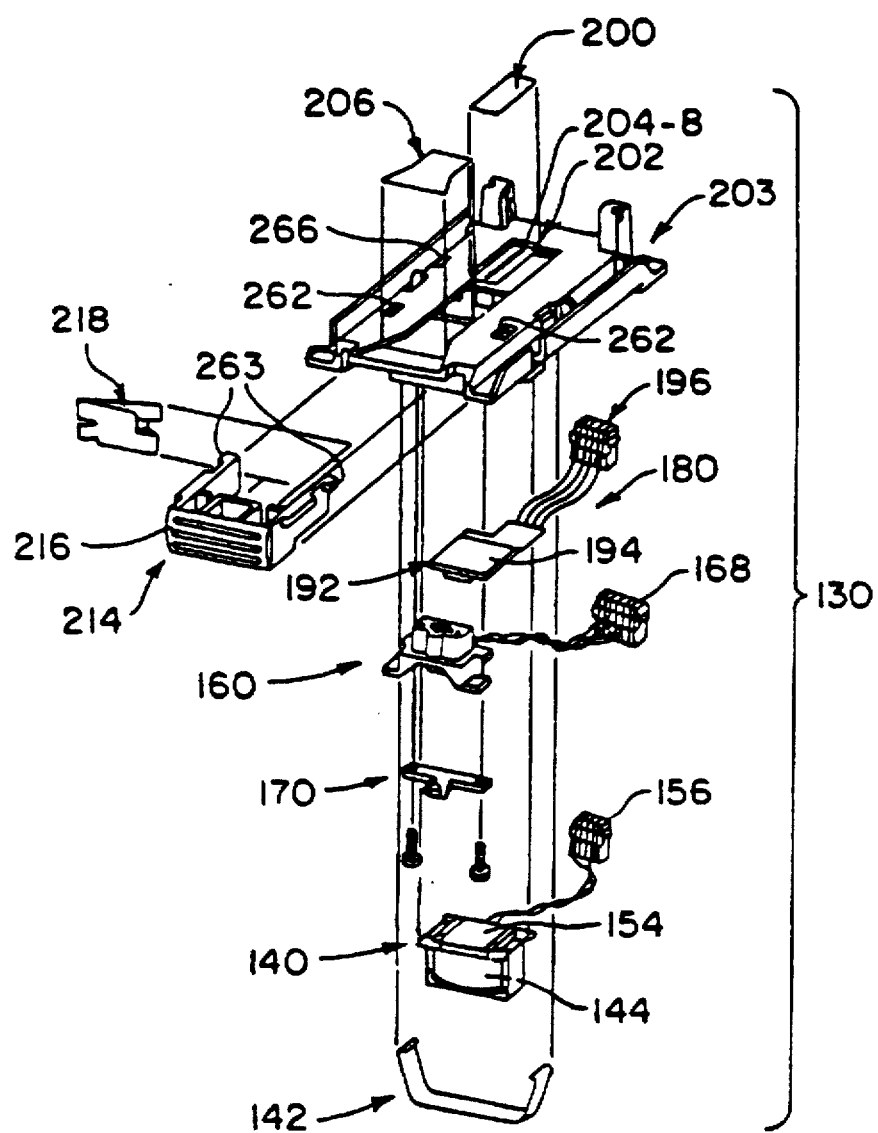
FIG. 5 illustrates an exploded perspective views of a detail of FIGS. 4.
Figure 6:
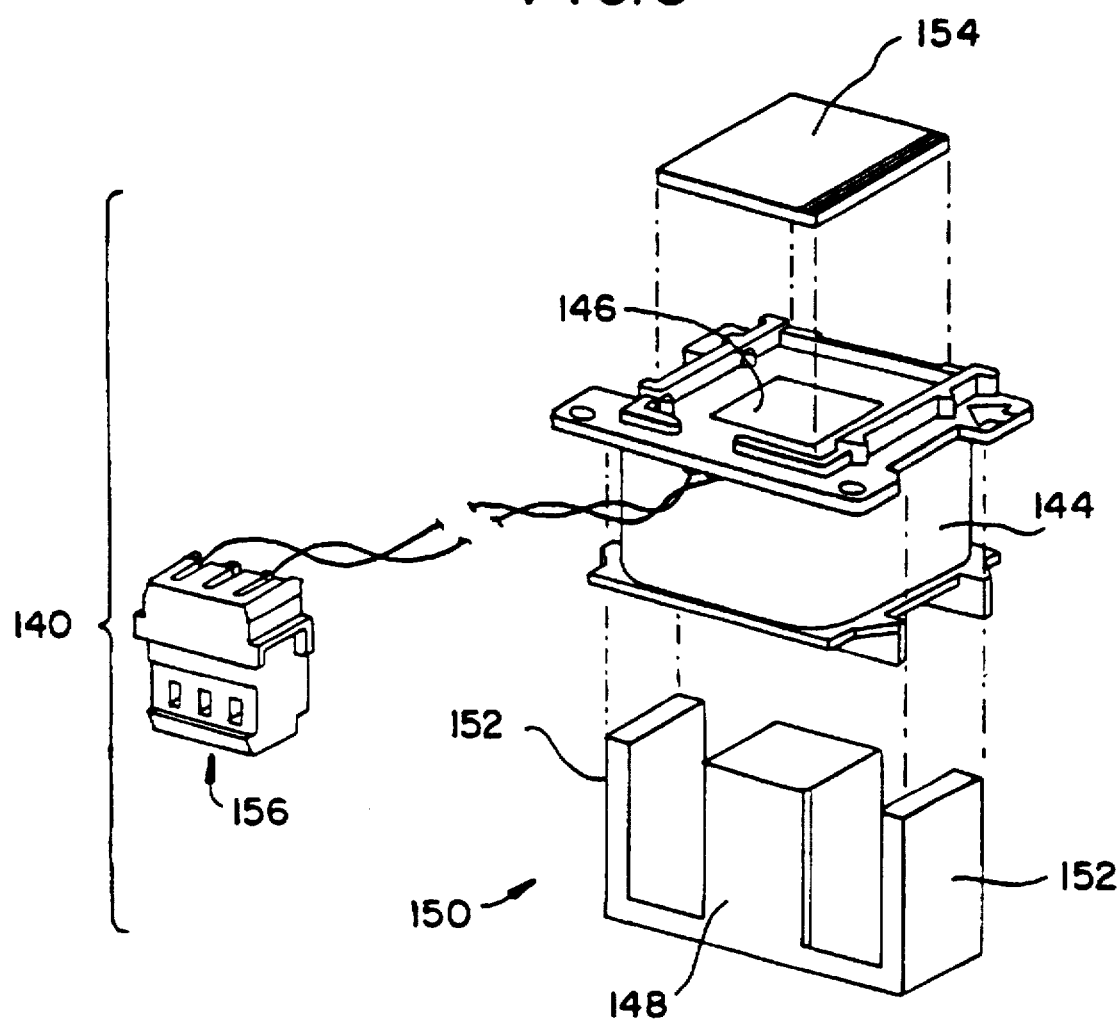
FIG. 6 illustrates an enlarged exploded perspective view of a detail of FIG. 5.
Figure 7A:
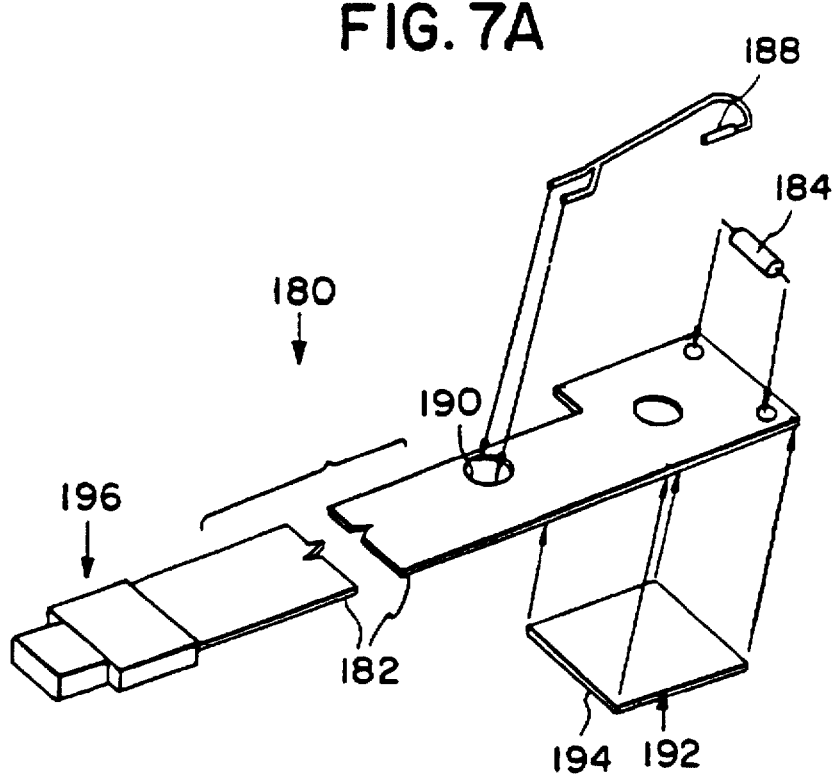
Figure 7B:
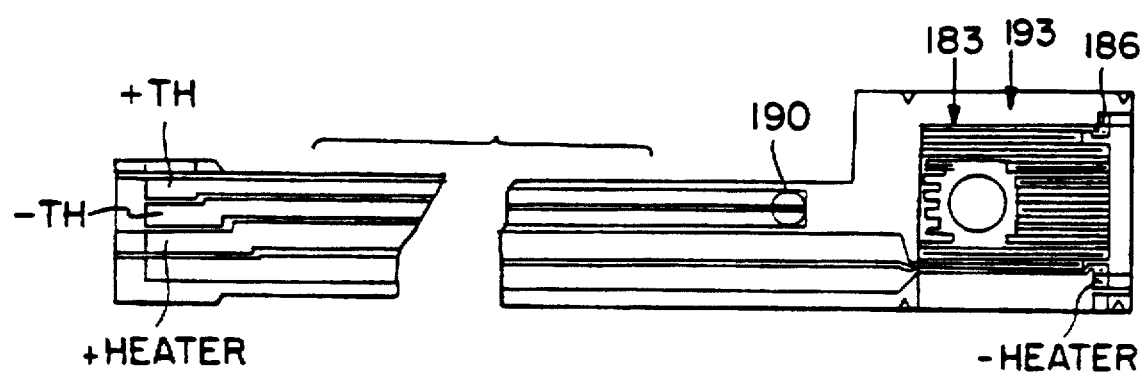
Figure 13:
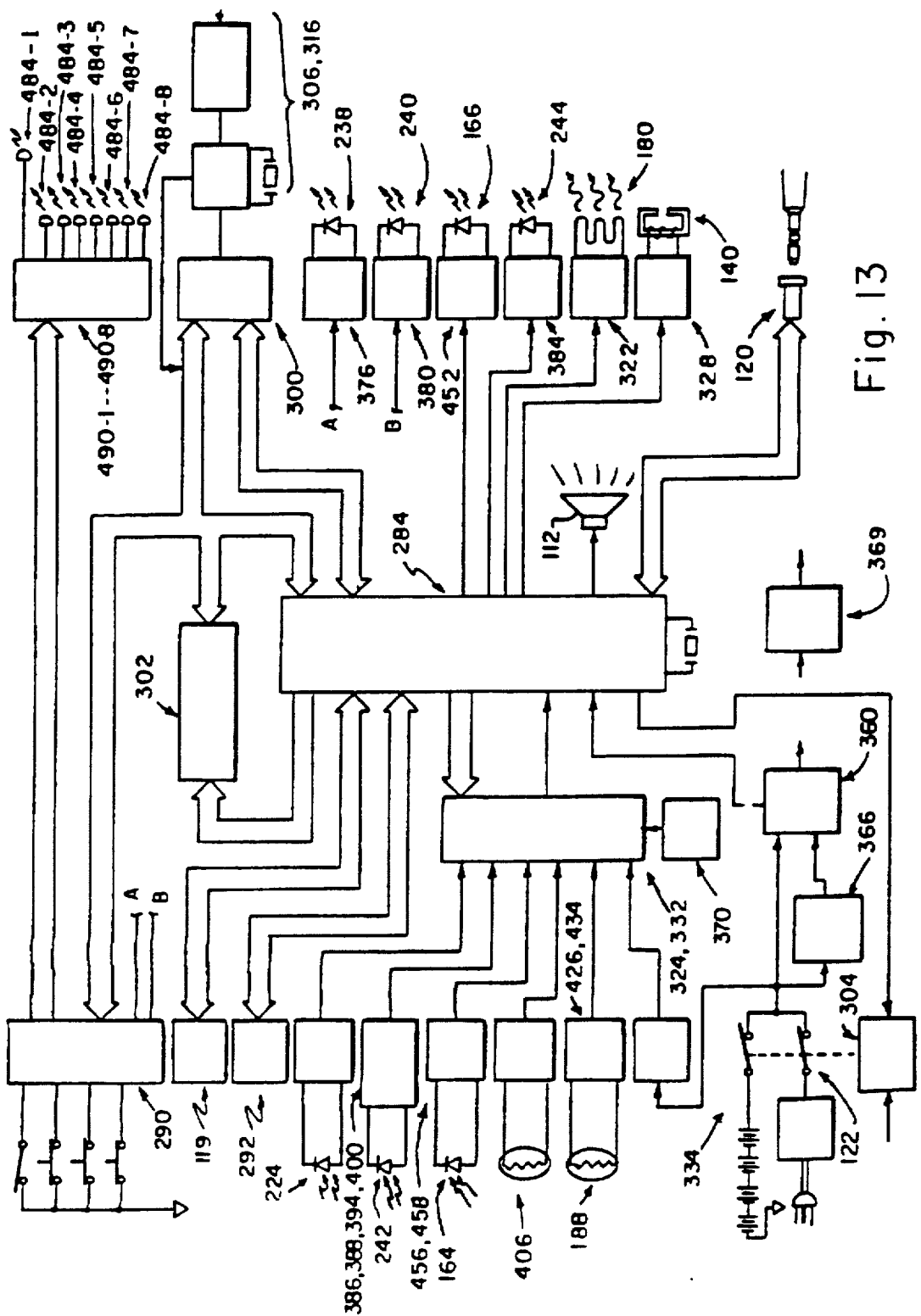
Figure 14:
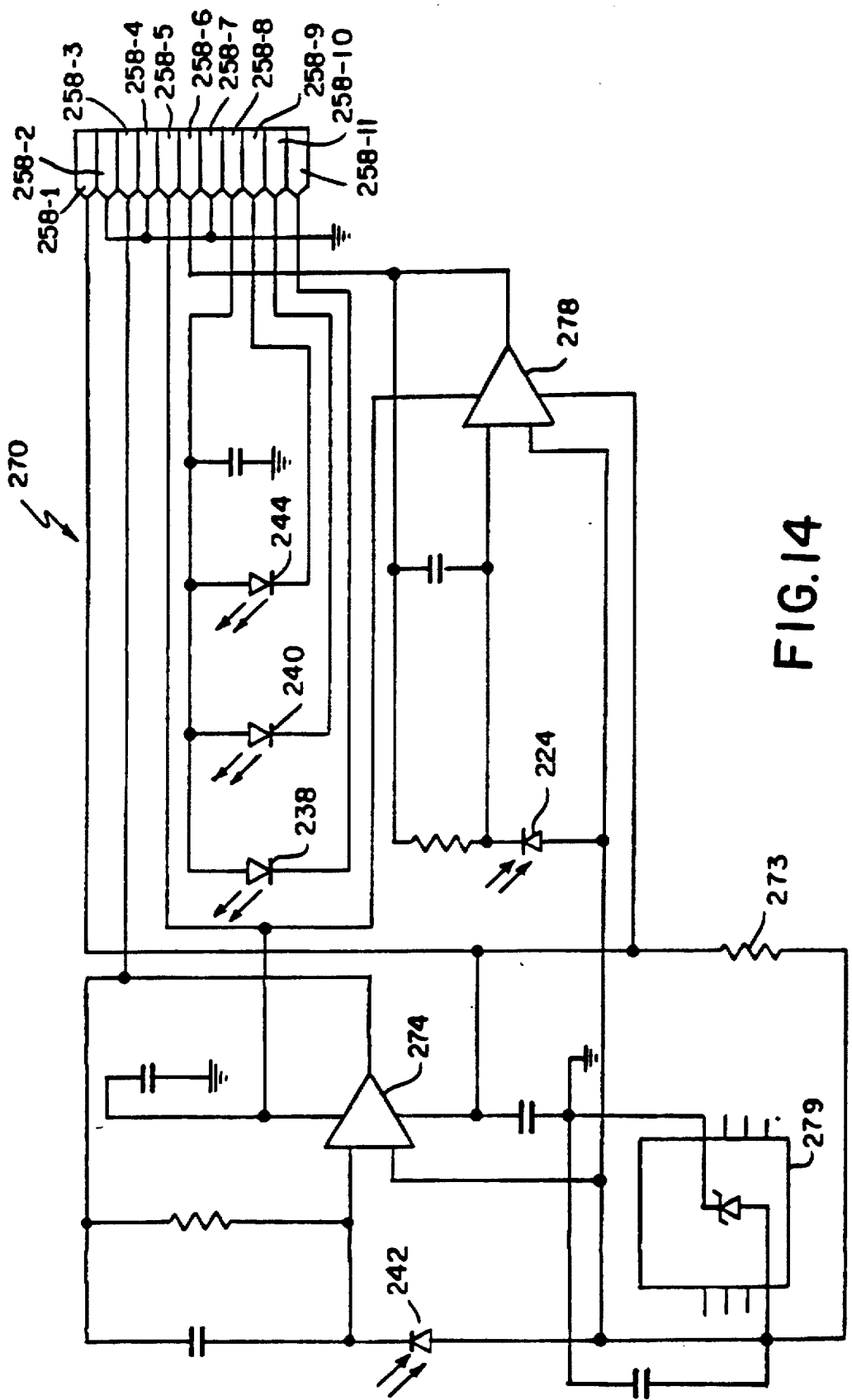
Figure 15A:
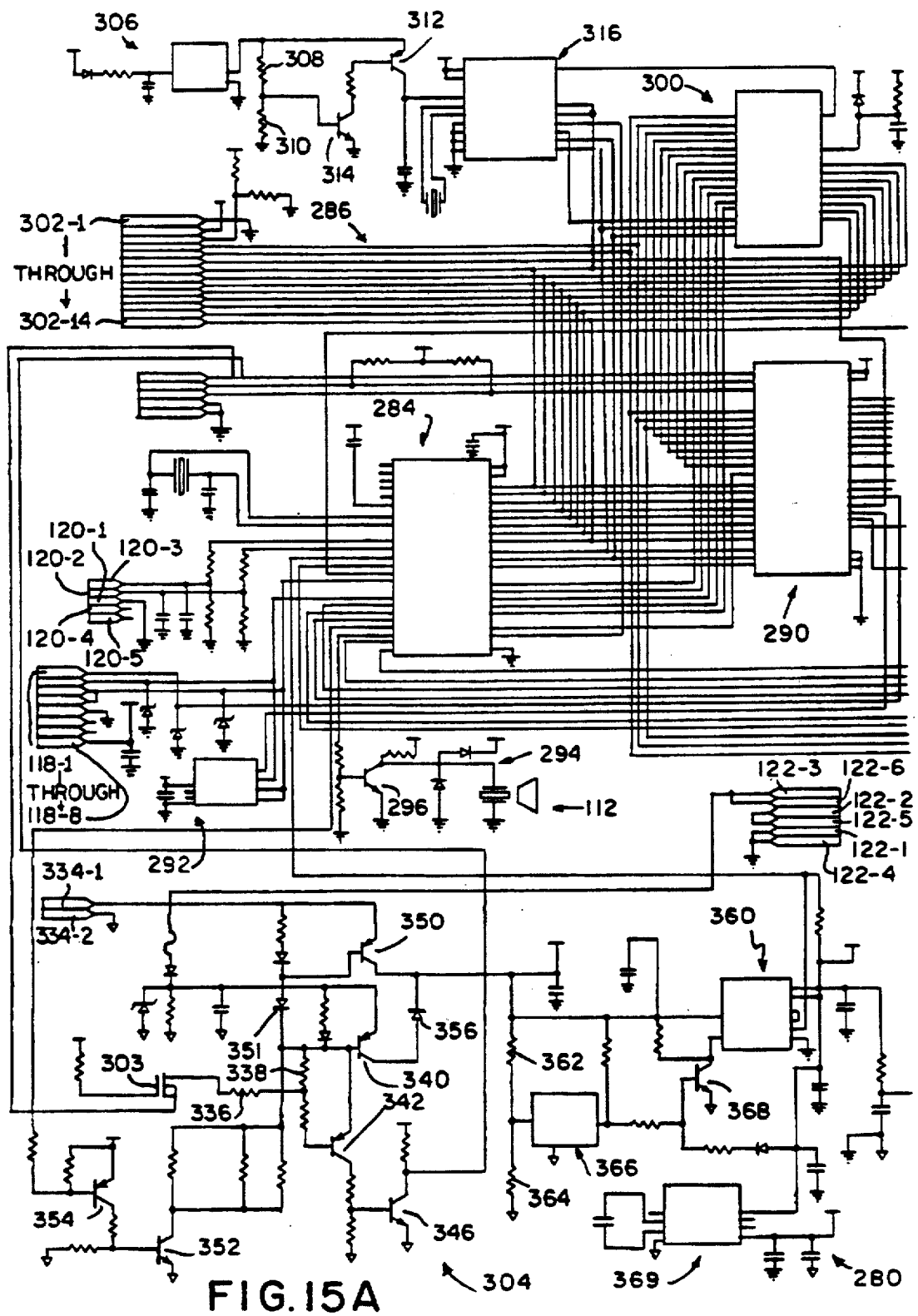
Figure 15B:
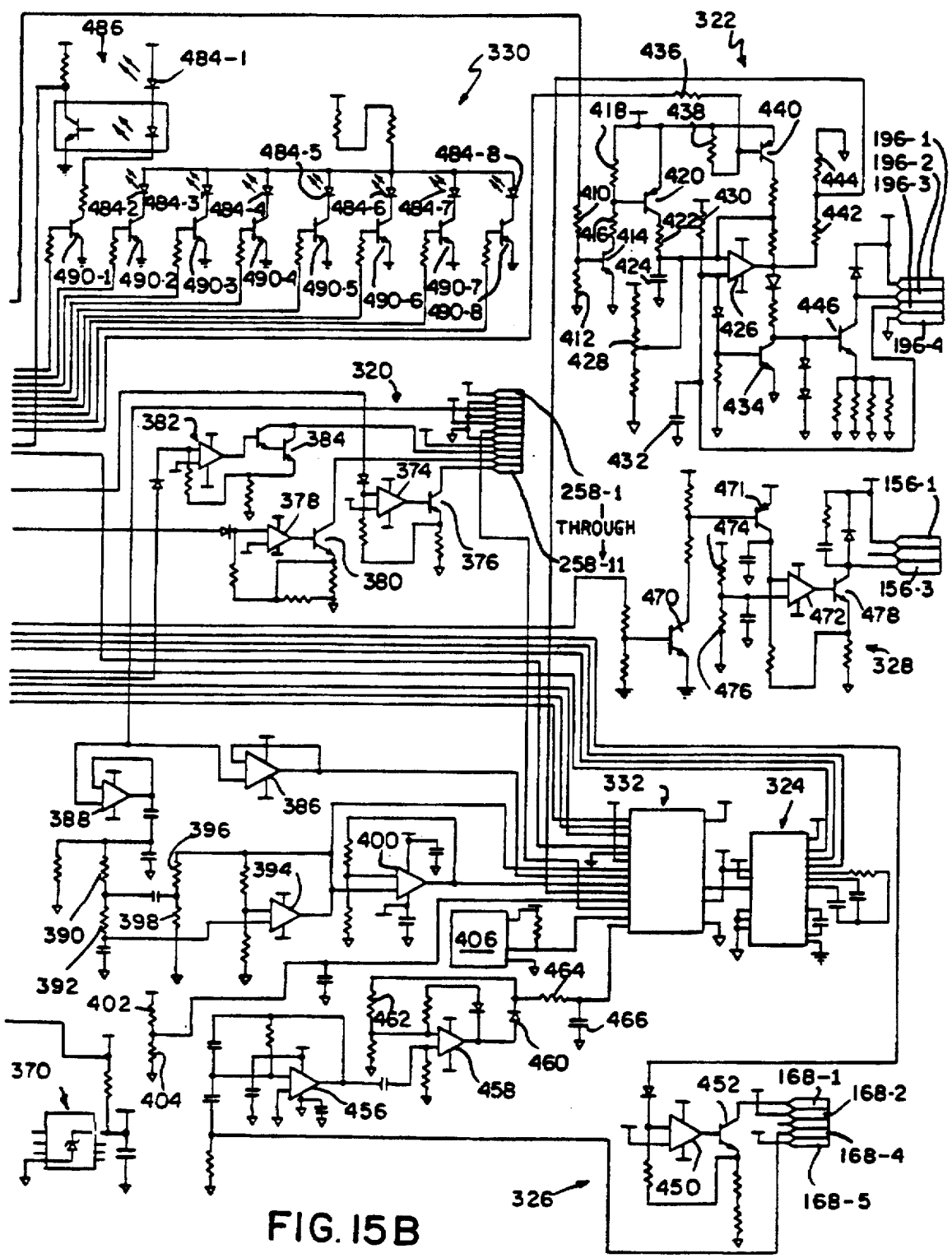
Figure 16:
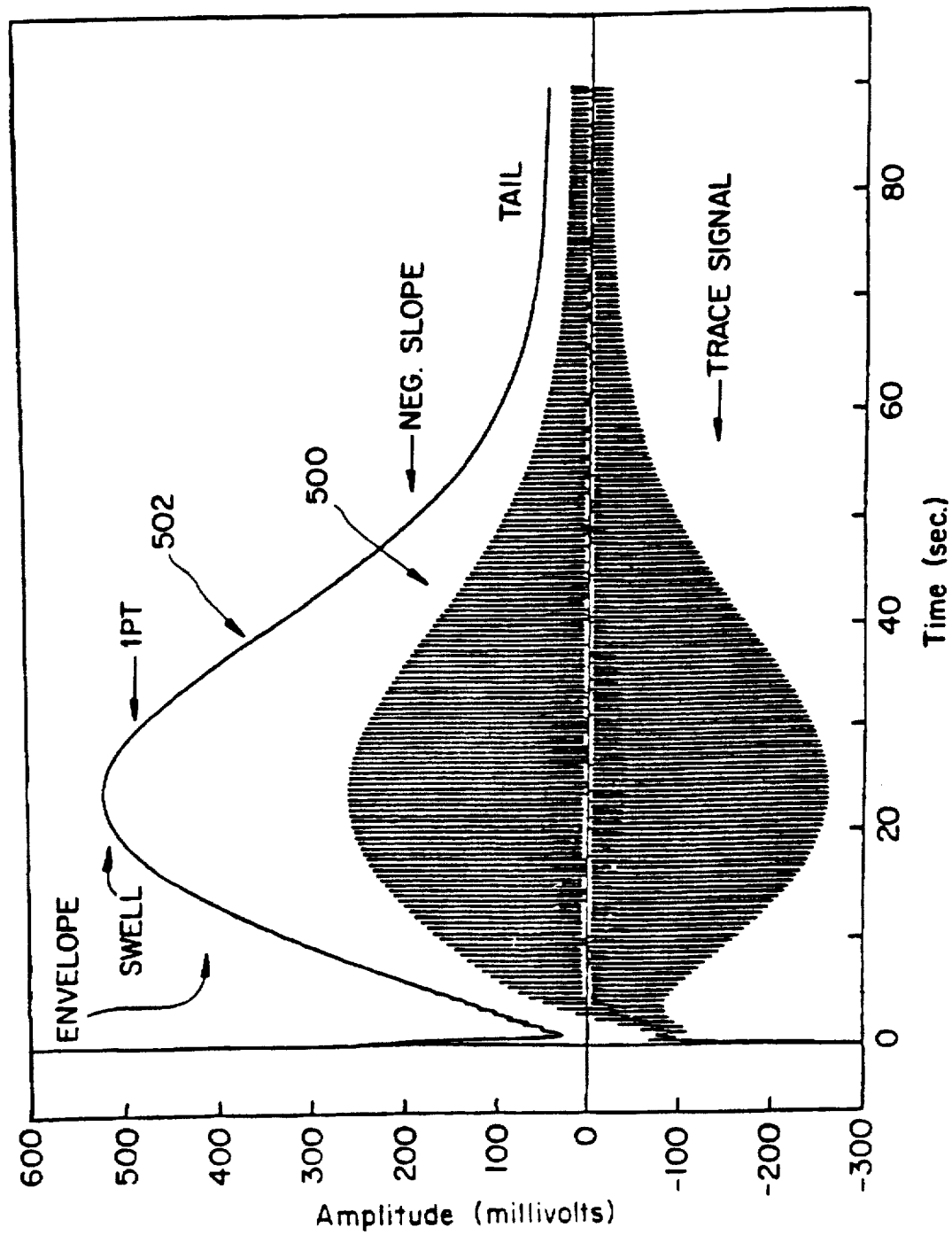
Figure 17A:
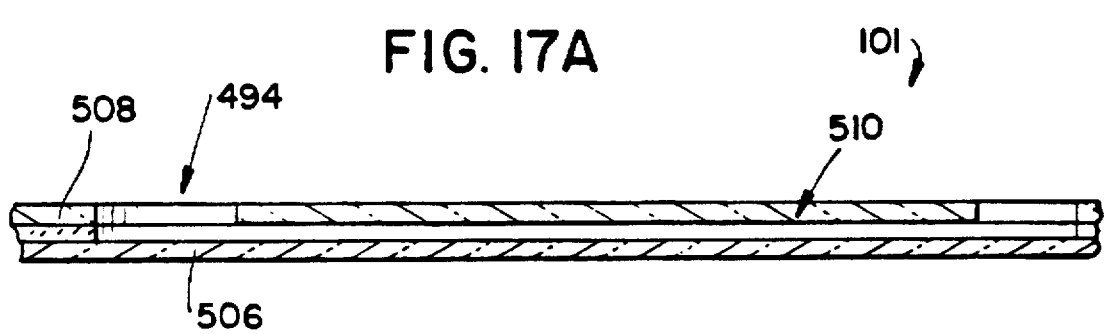
Figure 17B:
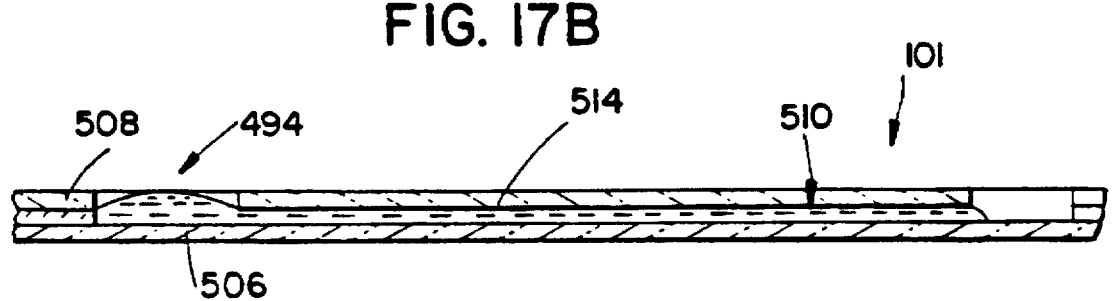

FIG. 7a–b illustrate an enlarged, fragmentary, exploded perspective view and a fragmentary bottom plan view, respectively, of a detail of FIG. 5;

FIGS. 8a–c illustrate a top perspective view, a different top perspective view, and a bottom perspective view, respectively, of a detail of FIG. 5;

FIGS. 9a–b illustrate an exploded bottom perspective view and an exploded top perspective view, respectively, of a detail of FIG. 5;

FIG. 10 illustrates a top plan view of a detail of FIG. 5;

FIGS. 11a–d illustrate exploded perspective views of details of FIG. 4;

FIGS. 12a–b illustrate perspective views from two different perspectives of a detail of FIG. 4;

FIG. 13 illustrates a block diagram of the electrical system of the instrument of FIG. 1;

FIG. 14 illustrates a schematic diagram of an an electric circuit of the instrument of FIGS. 1 and 13;

FIGS. 15a–b illustrate a schematic diagram of an electric circuit of the instrument of FIGS. 1 and 13;

FIG. 16 illustrates a reflected light signal and a rectified reflected light envelope according to the present invention;

FIGS. 17a–b illustrate enlarged fragmentary longitudinal sectional views taken generally along section lines 17—17 of FIG. 4;

FIG. 18 illustrates a detected light profile according to the present invention.

Figure 19:
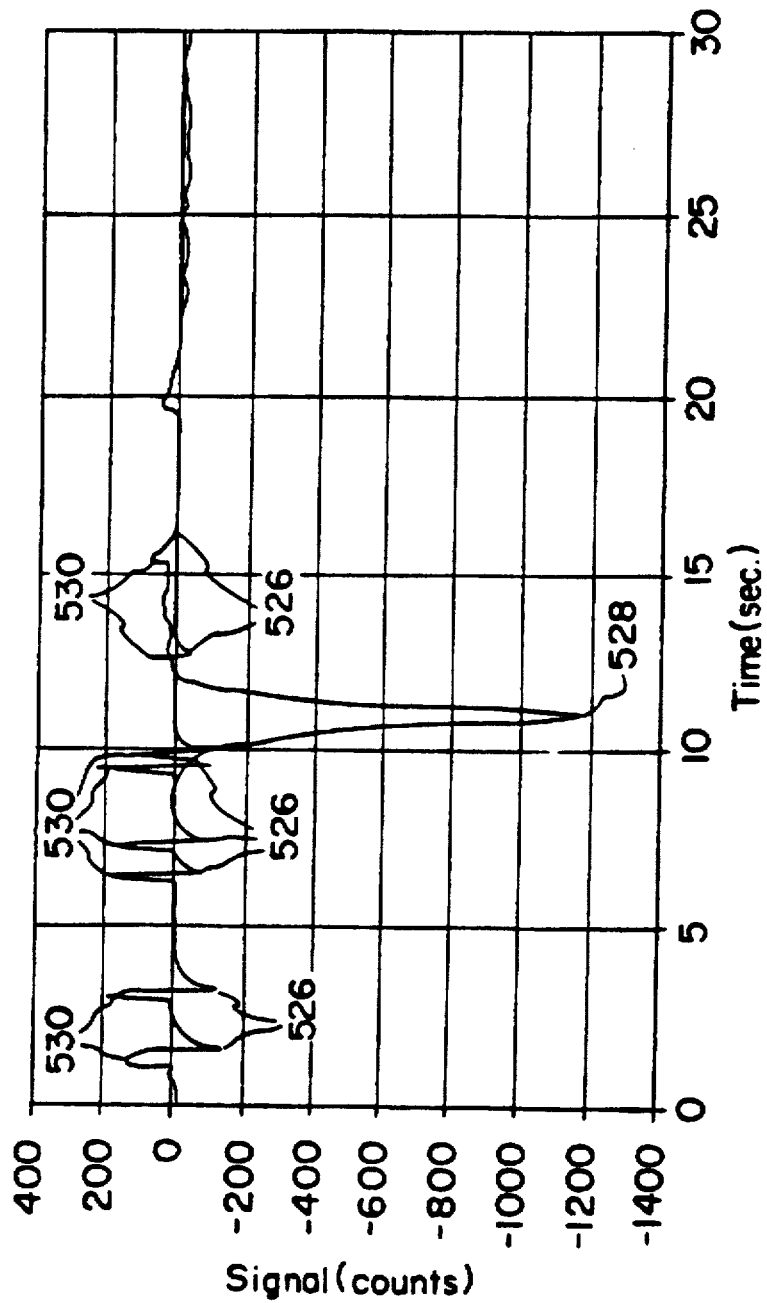

FIG. 19 illustrates the noise immunization technique of the present invention.

The following schematic and block circuit diagram descriptions identify specific integrated circuits and other components and in many cases specific sources for these. Specific terminal and pin names and numbers are generally given in connection with these for the purposes of completeness. It is to be understood that these terminal and pin identifiers are provided for these specifically identified components. It is to be understood that this does not constitute a representation, nor should any such representation be inferred, that the specific components or sources are the only components available from the same or any other sources capable of performing the necessary functions. It is further to be understood that other suitable components available from the same or different sources may not use the same terminal/pin identifiers as those provided in this description.

An instrument 100 for determining the coagulation time of a specimen, whether of blood or of a control, includes a housing 102 comprising a housing bottom 104 and a housing top 106. Top 106 is provided with a battery door 108 which covers a battery well 110 housing the instrument 100's battery power source (not shown). Bottom 104 houses a piezoelectric beeper 112, and a printed circuit board (PCB) 114 onto which are assembled various circuit components which will be described later. An optics assembly 116, a socket 118 for a test parameters electronically erasable programmable read-only memory (EEPROM) key 119 of the type described in U.S. Pat. No. 5,053,199, a socket 120 for serial data communication, and a power supply connector 122 for connection of instrument 100 to an external AC/DC adapter (not shown) for operation thereby in lieu of the batteries (not shown) with which instrument 100 is typically equipped, are also assembled onto PCB 114.

Optics assembly 116 includes a covered 126 strip adapter top assembly 132 hinged 128 to a strip adapter bottom assembly 130. Strip adapter bottom assembly 130 includes a magnet assembly 140 held to bottom assembly 130 by a spring clip retainer 142. Magnet assembly 140 includes a coil 144 wound on a bobbin 146 which is positioned over the center leg 148 of an E-core 150. The end legs 152 of E-core 150 lie outside coil 144. A bias magnet 154 is placed over the end of the center leg 148 and is supported on one end of the bobbin 146. A connector 156 permits electrical connections to be made to coil 144.

Strip adapter bottom assembly 130 also includes a sample port housing assembly 160 having a housing 162 within which are mounted a photodiode 164 and a LED 166. Photodiode 164 senses light generated by LED 166 and reflected from the sample and strip 101 to provide an indication that a sample, be it blood or control, has been applied to instrument 100 for testing. A connector 168 provides for electrical connections to photodiode 164 and LED 166. A clamp 170 retains LED 166 in housing 162. The angle between the axes of the LED 166 and photodiode 164 openings 172, 174, respectively, is about 15°.

Strip adapter bottom assembly 130 also includes a heater assembly 180 including a heater foil 182 constructed from two polyamide films between which is sandwiched a foil trace 183. A thermal fuse 184 and a thermistor 188 are mounted on the side of the foil 182 opposite the heater trace. Thermal fuse 184 is coupled through the foil 182 between one terminal 186 of the heater foil trace and the − HEATER terminal of a heater circuit. Contact is made to the leads of thermistor 188 from the THermistor + and − leads of the heater circuit through a hole 190 in the foil 182. An aluminum nitride heater plate 192 having a light reflecting top surface 194 is attached to foil 182 over the heater pattern area 193 of the heater trace using a thermosetting acrylic adhesive. Electrical connections are made to heater assembly 180 through a connector 196.

A transparent polycarbonate window 200 is adhesively attached to a region 202 of strip adapter bottom assembly housing 203 which is formed with a series of eight transversely extending slit openings 204-1–204-8, respectively. A transparent polycarbonate window 206 is provided with an opaque glossy black coating 208 over part of its surface and an opaque glossy yellow coating 210 over part of its surface. The remainder 211 of window 206 remains transparent. Remainder 211 overlies a slit 213 in housing 203 through which radiation from LED 166 is transmitted to the sample and through which remission from the sample is detected by photodiode 164. The yellow region 210 visible to the user of instrument 100 indicates where the sample, be it blood or control, is to be placed on a transparent disposable strip 101, such as those illustrated and described in U.S. Pat. No. 4,849,340 or the CoaguChek™ coagulation system test strip available from Boehringer Mannheim Corporation, 9115 Hague Road, Indianapolis, Ind. 46250, when the disposable strip 101 is properly located in the optics assembly 116. A push-button latch 214 including a button 216 biased into locking position by a scissors-shaped compression spring 218 completes strip adapter bottom assembly 130.

Strip adapter top assembly 132 includes a strip adapter top 222 into which is mounted a bar code reading photodiode 224 with an elongated active region exposed through a slot 226 and a transparent polycarbonate window 228 adhesively mounted on the underside of top 222 to close slot 226. A photosensor bracket 230 captures photodiode 224 in position adjacent slot 226. Test strip clamps containing foam springs 232, useful in pressing test strip 101 against heater plate 192, have tabs that fit into locating openings provided therefor in the floor of top 222. Space 235 is provided between clamps 232 to accommodate a positioning bracket 236 which is mounted on the underside of PCB 234 and extends downward therefrom into space 235. START LED 238 and FILL LED 240 are mounted respectively in front of and behind positioning bracket 236 angled at about 5° to the normal plane of incidence on PCB 234. A photodiode 242 with a daylight filter is mounted on PCB 234 inside positioning bracket 236. All three of components 238, 240, 242 are exposed downward through openings provided therefor in the bottom of strip adapter top 222 of the strip adapter top assembly 132. A MAIN assay LED 244 is mounted in an opening 246 provided therefor in strip adapter top 222 and is held in place by a holding clamp 248. The leads of LED 244 are connected to PCB 234. The axis of opening 246 makes an angle of about 45° with the axis of the opening for photodiode 242 and intersects it.

A pop-up bracket 250 is spring 252-loaded into an opening provided therefor in a rear end wall 254 of strip adapter top 222 to cause the strip adapter top assembly 132 to pop up when button 216 is pushed. An eleven-conductor flat-cable 256 and connector 258 make the connections between the components mounted on PCB 234 and the remaining circuits of the PCB 114. Pawl-type catches 260 extend downward from the two forward corners of strip adapter top 222. Openings 262 are provided adjacent the front corners of strip adapter bottom assembly 130 to accommodate catches 260. Cooperating tongues 263 on button 216 are urged into engagement with catches 260 by spring 218 when strip adapter bottom assembly 130 and top assembly 132 are closed together. A flag 264 which extends downward from a side edge of strip adapter top 222 extends into a slot 266 provided for this purpose in strip adapter bottom assembly 130 where flag 264 interrupts a light path from a source to a detector to indicate that the strip adapter top and bottom assemblies 132, 130, respectively, are closed together.

The electrical circuitry on PCB 114 powers and reads the various sensors included on the coagulation optics circuit 270 on PCB 234. +5V and −5V are supplied to circuit 270 through terminals 258-5 and 258-1, respectively, of connector 258. Unregulated voltage is supplied to terminal 258-8 of connector 258. Ground for circuit 270 is provided at terminals 258-2, 4 and 7 of connector 258. A capacitor is coupled across terminals 258-8 and 258-2, 4, 7. The anodes of LEDs 238, 240, 244 are all coupled to terminal 258-8. The cathode of LED 238 is coupled to the START terminal, terminal 258-11, of connector 258. The cathode of LED 240 is coupled to the FILL terminal, terminal 258-10, of connector 258. The cathode of LED 244 is coupled to the MAIN terminal, terminal 258-9, of connector 258.

The anodes of photodiodes 224, 242 are coupled through a resistor 273 to terminal 258-1. The cathode of photodiode 242 is coupled to the − input terminal of an operational amplifier 274. The + input terminal of operational amplifier 274 is coupled to the anodes of photodiodes 224, 242. The output terminal of operational amplifier 274 is coupled to its − input terminal through a parallel RC feedback circuit. The output terminal of operational amplifier 274 is also coupled to the DETect terminal, terminal 258-3, of connector 258.

The cathode of photodiode 224 is coupled to the − input terminal of an operational amplifier 278. The + input terminal of operational amplifier 278 is coupled to the anodes of photodiodes 224, 242. The output terminal of operational amplifier 278 is coupled to its − input terminal through a parallel RC feedback circuit. The output terminal of differential amplifier 278 is also coupled to the CodeBaR OUTput terminal, terminal 258-6, of connector 258.

A +V terminal of a 2.5V reference voltage source 279 is coupled to terminals 258-2, -4 and -7 of connector 258. The − terminal of reference voltage source 279 is coupled to the anodes of photodiodes 224, 242, to the + input terminals of operational amplifiers 274, 278, and through resistor 273 to the −5V terminal, 258-1, of connector 258.

The electric circuitry 280 mounted on PCB 114 processes the various signals from circuitry 270, as well as others which circuitry 280 generates itself or receives from the user of instrument 100, or which are generated externally to instrument 100. An Intel type N83C51FC eight-bit microcontroller (AC) 284 has data terminals P0.0–P0.7 coupled to DATA lines 0–7, respectively, of an instrument 100 bus 286.

μC 284 address terminals P2.0–P2.4 and P2.6–P2.7 are coupled to address lines A8–A12 and A14–A15, respectively, of bus 286. The $\overline{\text{ReaD}}$ and $\overline{\text{WRite}}$ terminals, P3.7 and P3.6, respectively, of μC 284, are coupled to the Read Data and Write Data lines, respectively, of bus 286. An Address Latch Enable terminal of μC 284 is coupled to the ALE terminal of a Toshiba type TC11L003AU-1031 application specific programmable gate array integrated circuit (ASIC) 290. The TIP (transmit) terminal 120-2 of serial data port socket 120 is coupled through the parallel combination of a capacitor and a resistor to ground, and through a series resistor to the Transmit Data (TXD) terminal P3.1 of μC 284. The RING (receive) terminal 120-3 of serial data port socket 120 is coupled through the parallel combination of a capacitor and a resistor to ground and through a series resistor to the Receive Data (RXD) terminal P3.0 of μC 284. The GrouND terminal 120-1 of socket 120 is coupled to ground.

The CS terminal 118-1 of ROM key socket 118 is coupled through a 6.2V Zener diode to ground and directly to a Code ROM IC chip Select OutPut terminal 22 of ASIC 290. The SK terminal, 118-2, of ROM key socket 118 is coupled through a Zener diode to ground and directly to the CLOCK terminal, terminal P1.0, of μC 284. It is also coupled to the SK terminal of an EEPROM 292 internal to instrument 100. EEPROM 292 generally contains the meter 100 characterizing parameters. The DI and DO terminals, terminals 118-3 and 4, of socket 118 are coupled to each other, to ground through a Zener diode, directly to the DI and DO terminals of EEPROM 292, and directly to the EEDI/DO terminal P3.5, of μC 284. Terminal 118-5 of socket 118 is coupled to ground. Terminal 118-8 of socket 118 is coupled to the system +5V supply.

The time base for μC 284 is generated by a 7.3728 MHz crystal which is coupled across terminals X1–X2 thereof. A capacitor is coupled between each terminal of the crystal and ground. Terminal P1.5 of μC 284 is coupled to a resistive voltage divider in a beeper 112 driver circuit 294. The common terminal of the series resistors is coupled to the base of a driver transistor 296. The collector of transistor 296 is coupled through a pull-up resistor to +5V and directly to one terminal of beeper 112. The emitter of transistor 296 and the other terminal of beeper 112 are both coupled to ground. Two diodes clamp the collector of transistor 296 between ground and +5V.

The data terminals D0–D7 of an 8K by 8 static random access memory (SRAM) 300 are coupled to the DATA 0-DATA 7 lines, respectively, of bus 286. The address terminals A0–A12 of SRAM 300 are coupled via the system bus 286 to the A0–A7 terminals of ASIC 290 and the A8–A12 terminals of μC 284, respectively. The $\overline{\text{ReaD}}$ and $\overline{\text{WRite}}$ terminals of SRAM 300 are coupled via the bus 286 to the $\overline{\text{ReaD}}$ and $\overline{\text{WRite}}$ terminals, respectively, of μC 284. The CE2 terminal of SRAM 300 is coupled to the junction of a resistor and a capacitor. The other terminal of the resistor is coupled to +5V. The other terminal of the capacitor is coupled to ground. The CE2 terminal is clamped via a diode to +5V. The DATA 0–DATA 7 terminals of a two line by sixteen character display 302 are coupled to the DATA 0–DATA 7 terminals of bus 286. The DISPlay ENable terminal of display 302 is coupled via bus 286 to the DISPlay ENable terminal of ASIC 290. The A0–A1 terminals of display 302 are coupled to the A0–A1 terminals, respectively, of bus 286. The GrouND terminal of display 302 is coupled to the system ground and the VDD terminal of display 302 is coupled to +5V. Terminal 3 of display 302 is coupled through a resistor to ground and through a resistor to +5V. An instrument 100 keypad switch has its ON/OFF terminal connected to the source of a field effect transistor (FET) 303 in instrument 100's power supply circuit 304. The YES terminal of the switch is coupled to InPut terminal 1 of ASIC 290. The NO terminal of the switch is coupled to InPut terminal 2 of ASIC 290. The YES and NO terminals are also coupled through respective pull-up resistors to +5V.

Battery back-up protection is provided to SRAM 300 by a circuit including a Ricoh type RH5RA33ATI 3.3V regulator 306. The $V_{in}$ terminal of regulator 306 is coupled to the junction of a 6.2Ω resistor and a 0.1 μF capacitor. The other terminal of the capacitor is coupled to ground. The other terminal of the resistor is coupled to the cathode of a type LL4148 diode, the anode of which is coupled to +VBAT. The $V_{out}$ terminal of regulator 306 is coupled across a series resistive voltage divider including a 7.5MΩ resistor 308 and a 2MΩ resistor 310 to ground. $V_{out}$ is also coupled to the emitter of a Siemens type BC858C PNP transistor 312. The junction of resistors 308, 310 is coupled to the base of a type BC848C NPN transistor 314. The emitter of transistor 314 is coupled to ground. Its collector is coupled through a 1MΩ series resistor to the base of transistor 312. The collector of transistor 312 is coupled to the BATtery 1 terminal of a Dallas Semiconductor type DS1215S real time clock 316, and to one terminal of a 0.1 F, 5.5V capacitor, the other terminal of which is coupled to ground. The D and Q terminals of IC 316 are coupled to the DATA 0 line of bus 286. The $\overline{\text{CEI}}$, $\overline{\text{CEO}}$, $\overline{\text{WE}}$ and $\overline{\text{OE}}$ terminals of IC 316 are coupled to terminal P2.7(A15) of μC 284, terminal $\overline{\text{CE}}$ of SRAM 300, the Write Data line of bus 286, and the Read Data line of bus 286, respectively. The VCC OUTPUT terminal of IC 316 is coupled to the VDD terminal of SRAM 300. The time base for IC 316 is generated by a 32.768 KHz crystal coupled across terminals X1–X2 thereof.

The PoWeR INTerrupt, MAIN ConTroL, HeaTeR ON/OFF, A/D OUT, A/D A, A/D B, power SUPPLY ON, SAMPLE ConTroL, and MAGnet 1 ConTroL terminals, terminals P3.2, P3.3, P3.4, P1.1, P1.2, P1.3, P1.4, P1.6 and P1.7, respectively of μC 284, are coupled to the power supply circuit 304, the main LED driver in an LED driver circuit 320, the heater control circuit 322, the COMParator OUTput terminal of a Teledyne type TSC500ACOE A/D converter IC 324 in the analog section of instrument 100, the A terminal of A/D 324, the B terminal of A/D 324, power supply circuit 304, the sample port circuit 326, and the magnet current control circuit 328.

The InPut 3 terminal of ASIC 290 is coupled to an optical switch 486. The OutPut 10–17 terminals of ASIC 290 are coupled to the bar code LED array driver circuit 330. The OutPut terminals 20, 21, 24 and 25 of ASIC 290 are coupled to the setpoint temperature control of heater driver circuit 322, the LATCH ENABLE terminal of a eight-to-one analog multiplexer 332 in the analog section of instrument 100, the fill LED driver in circuit 320, and the start LED driver in circuit 320, respectively. The Address 0–2 lines of bus 286 are coupled to the A, B and C terminals, respectively, of multiplexer 332.

Power supply circuit 304 includes an instrument 100 battery connector 334 having +VBAT terminal 334-1 and ground terminal connector 334-2 and AC/DC converter power supply connector 122 having +VIN terminals 122-3 and 6 connected together and GRouNd terminals 122-1 and 4 connected together. +VBAT is coupled through a 1MΩ series resistor to the gate of FET 303. The drain of FET 303 is coupled through two series 200 Ω resistors 336, 338 to the base of a Samsung type MJD2955 PNP transistor 340. The emitter of transistor 340 is coupled to its base through the series combination of a 10KΩ resistor and a type LL4148 diode, through a type LL5819 diode and 2.0 ampere fuse to +VIN, and through a parallel combination of a General Instruments type 1.5KE18P transient suppressor diode, a 10KΩ resistor and a 1000 μF, 25V capacitor to ground. The junction of resistors 336, 338 is coupled through a 10KΩ resistor to the base of a type BC858C PNP transistor 342. The emitter of transistor 342 is coupled to the base of transistor 340. The collector of transistor 342 is coupled through two series 100KΩ resistors to ground. The common terminal of these 100KΩ resistors is coupled to the base of a type BC848C NPN transistor 346. The emitter of transistor 346 is coupled to ground and its collector is coupled through a 1MΩ pull-up resistor to +5V. The collector of transistor 346 is also coupled to InPut terminal 0 of ASIC 290.

The emitter of a type MJD2955 PNP transistor 350 is coupled to +VBAT. +VBAT is coupled through a 10KΩ resistor and a type LL4148 diode in series to the base of transistor 350. The base of transistor 350 is coupled through a type LL4148 diode 351 to the base of transistor 340. The base of transistor 340 is coupled through a parallel resistance network having an effective resistance of about 450 Ω to the collector of a type BC848C NPN transistor 352. The emitter of transistor 352 is coupled to ground. Its base is coupled through a 10KΩ resistor to ground and through a 10KΩ resistor to the collector of a type BC858C transistor 354. The emitter of transistor 354 is coupled to +5V Analog. The base of transistor 354 is coupled through a 100KΩ resistor to +5VA. The base of transistor 354 is also coupled through a 100KΩ resistor to terminal P1.4 of μC 284. Once the on/off key to meter 100 is depressed upon turn-on, enough time is given for the +5V supply to come up and the μC 284 to reset itself (once +5V supply has been applied to its $V_{CC}$ pin) and then to have terminal P1.4 of μC 284 latch the system +5V supply on. This terminal is also used to shut the system down in an orderly fashion. VUNREGulated appears at the collector of transistor 350 and at the cathode of a type LL5819 diode 356, the anode of which is coupled to the collector of transistor 340.

Regulation is initiated by battery voltage +VBAT on the gate of FET 303. If the battery is in backward, or is below minimum regulation level and no AC/DC adapter is connected to instrument 100, or is missing and no AC/DC adapter is connected to instrument 100, the instrument 100 cannot be turned on. If the battery is installed properly and is above minimum regulation level, regulation is established at the base of transistor 340 and, through diode 351, at the base of transistor 350. Regulation is also signalled through transistors 342 and 346 to the ON/OFF INDicator InPut terminal 0 of ASIC 290. If the battery voltage +VBAT is greater than +VIN, diode 356 decouples the AC/DC adapter input circuitry, including transistor 340 and its associated regulating circuitry from VUNREGulated so that the battery does not power that circuitry.

VUNREGulated is supplied to the VIN terminal of a National Semiconductor type LP2951M +5V regulator IC 360. VUNREGulated is also supplied to a series voltage divider including a 20KΩ, 1% resistor 362 and a 100KΩ, 1% resistor 364. The common terminal of resistors 362, 364 is coupled to the INput terminal of a Seiko type S-80745AN-D9-X voltage detector IC 366. The ERROR output terminal of IC 366 is coupled through a 100KΩ resistor to VUNREGulated and through a 100KΩ resistor to the base of a type BC848C NPN transistor 368. The collector of transistor 368 is coupled through a 100KΩ load resistor to VUNREGulated and is coupled directly to the SHUTDOWN terminal of +5V regulator IC 360. If the supply voltage is low, IC 366 will prevent instrument 100 from being turned on. Regulated +5V for the digital circuitry of instrument 100 appears at the VOUT terminal of +5V regulator IC 360. The SENSE terminal of IC 360 is coupled to +5v. The ERROR terminal of IC 360 is coupled through a 100KΩ pull up resistor to +5V. The ERROR terminal is also coupled to the PoWeRINTerrupt terminal, P3.2, of μC 284. The error terminal's main function is to warn the μC 284 that the system power is approaching an unregulated condition. By warning μC 284 of such condition, μC 284 can power down the system in an orderly fashion prior to any soft failures occurring. A 0.1 μF capacitor across VOUT and GrouND of IC 360 is decoupled by a 1 Ω resistor from a 100 μF, 6.3V tantalum capacitor across the +5 VAnalog supply to analog ground. The voltage across the VOUT output terminal to ground is fed back through a type LL4148 diode and 100KΩ resistor in series to the base of transistor 368. The VOUT output terminal of IC 360 is also coupled to the V+ terminal of a Linear Technology type LTC1044CS8 +5V-to--5V converter 369. A 10 μF, 6.3V tantalum capacitor is coupled across the CAP+ and CAP- terminals of converter 369. -5VDC for circuits requiring it appears across the VOUT terminal of converter 369 to ground. The instrument 100's analog and digital grounds are tied together here. A +V terminal of an LM385M-2.5, 2.5V reference voltage source 370 is coupled through a 15KΩ resistor to +5 VAnalog. 2.5 VREFerence is established across the +V terminal of source 370 and ground.

Thus, instrument 100 for determining a characteristic, such as a coagulation time, of a biological fluid, such as blood or a blood fraction, or a control comprises a slide 101 defining a cuvette 494, 510 for receiving a sample 514 of the biological fluid or control, the characteristic of which is determined in such a way that the characteristic is exhibited by the sample 514. Microcontroller 284 controls receiving the sample through sample port circuit 326 via analog multiplexer 332 and A/D converter 324. The sample 514 characteristic is monitored as illustrated in FIG. 16, and a result of the monitoring of the sample 514 is converted by the circuit of FIGS. 15a–b into the characteristic. Microcontroller 284 controls orderly de-energization of the instrument either through direct control signals to power supply circuit 304, LED driver circuit 320, bar code LED array driver circuit 330, heater driver circuit 322, magnet control circuit 328, optical switch 486, and sample port circuit 326, or through ASIC 290. Microcontroller 284 interfaces with ASIC 290 and SRAM 300 over bus 286.

In power supply circuit 304, an AC/DC converter provides an input power source to power supply circuit 304 through connectors 122-3, -6 and 122-1, -4. A battery provides a second input power source to power supply circuit 304 through connectors 334-1, 334-2.

Capacitors throughout the circuit of FIGS. 15a–b store sufficient energy to permit the controller to orderly de-energize the instrument. For example, a 0.1 F capacitor stores energy from the voltage output of 3.3 volt regulator 306 for supplying power to real time clock 316. Microcontroller 284 has associated with it capacitors which store energy on both its voltage supply inputs and its clock inputs. Power supply circuit 304 stores energy in capacitors coupled to the emitter of transistor 340, the collector of transistor 350, and the outputs of 5 volt regulator IC 360.

Power supply circuit 304 includes voltage detector 336 which monitors the input voltage to instrument 100 at the collector of transistor 350.

Voltage detector 336 is coupled to 5 volt regulator IC 360 through transistor 368 for signalling microcontroller 284 when input voltage to power supply circuit 304 falls below a predetermined threshold.

The AC/DC converter voltage connectors 122-3, -6 and battery voltage connector 334-1 are coupled to the voltage detector IC 336 through a network of resistors, diodes, and transistors 340, 350, 342, 346, 352, 354.

Illustratively, instrument 100 comprises a battery (not shown) provided in the instrument and coupled to power supply circuit 304 through input connectors 334-1, 334-2, and an AC-to-DC converter (not shown) for supplying an input voltage across connectors 122-3, -6, and 122-1, -4 with a voltage of a higher magnitude than the battery voltage when the converter is coupled to a line voltage source.

Illustratively, instrument 100 further comprises an ON/OFF switch for energizing the instrument. Power supply circuit 304 selectively couples one of the battery voltage across connectors 334-1 and 334-2 or the converter voltage across AC/DC converter connectors input 122-3, -6 and 122-1, -4 to instrument 100 through transistors 340, 350 and diode 356. Power supply circuit 304 also couples the ON/OFF switch to transistors 340, 350 through the gate of FET 303 and the intervening circuitry.

Microcontroller 284 is further coupled to the base of transistor 354 in power supply circuit 304. Voltage detector 366 and 5 volt regulator IC 360 signal microcontroller 284 if the monitored voltage does not exceed a threshold, whereupon microcontroller 284 inhibits energization of instrument 100.

Turning now to the LED driver circuitry 320 for the optical head assembly 116, the start LED control OutPut terminal 25 of ASIC 290 is coupled through a diode to the −input terminal of an operational amplifier 374. The +input terminal of operational amplifier 374 is coupled to VREF. The output terminal of operational amplifier 374 is coupled to the base of a transistor 376. The collector of transistor 376 is coupled to the START LED terminal, terminal 258-11, of connector 258. The emitter of transistor 376 is coupled to ground through a resistor, which limits the current through the start LED at a constant current, and through a feedback resistor to the −input terminal of operational amplifier 374.

The FILLConTroL terminal, OutPut terminal 24, of ASIC 290 is coupled through a diode to the −input terminal of an operational amplifier 378. The +input terminal of operational amplifier 378 is coupled to VREF. The output terminal of operational amplifier 378 is coupled to the base of a transistor 380, the collector of which is coupled to the FILL LED terminal, terminal 258-10, of connector 258. The emitter of transistor 380 is coupled through a parallel resistor network to ground, which limits the current through the fill LED at a constant current, and through a feedback resistor to the −input terminal of operational amplifier 378.

The MAIN ConTroL terminal, P3.3, of µC 284 is coupled through a diode to the −input terminal of an operational amplifier 382. The +input terminal of operational amplifier 382 is coupled to VREF. The output terminal of operational amplifier 382 is coupled to the base of a Darlington-coupled transistor pair 384. The collectors of transistors 384 are coupled to the MAIN assay LED terminal, 258-9, of connector 258. The emitter of transistors 384 is coupled through a resistor to ground, which limits the current through the main LED at a constant current, and through a resistor, to the −input terminal of operational amplifier 382.

The sensed bar code of the disposable test strip 101 which is being used in a particular test comes in to circuit 320 serially on the CodeBaR terminal, 258-6, of connector 258. It is coupled directly to analog input terminal X5 of multiplexer 332. The START, FILL and MAIN assay DETect signals indicating that an adequate volume sample droplet has been placed over yellow area 210 on a test strip 101, and its raw coagulation results data, are provided from terminal 258-3 of connector 258 to the +input terminals of two operational amplifiers 386, 388. Operational amplifier 386 is configured as a unity gain buffer and its output terminal is coupled to the DC input terminal X1 of multiplexer 332. Operational amplifier 388 is also configured as a unity gain buffer and its output terminal is capacitively coupled through a capacitor and two series resistors 390, 392 to a +input terminal of an operational amplifier 394. The output terminal of operational amplifier 388 is also coupled to ground through an RC parallel combination. The + terminal of operational amplifier 394 is coupled to ground through a capacitor. The output terminal of operational amplifier 394 is coupled through a feedback resistor to its −input terminal. Its −input terminal is coupled to ground through a resistor. The output terminal of operational amplifier 394 is also coupled through series resistors 396, 398 to ground. The common terminal of resistors 396, 398 is coupled through a capacitor to the common terminal of resistors 390, 392.

The signal at the output terminal of operational amplifier 394 is directly coupled to the X0 input terminal, AC1, of multiplexer 332. That signal is also coupled to the +input terminal of an operational amplifier 400. The signal at the output terminal of operational amplifier 400 is directly coupled to the X2 input terminal, AC2, of multiplexer 332. The output terminal of operational amplifier 400 is also coupled through a resistor to the −input terminal thereof. The −input terminal of operational amplifier 400 is coupled through a resistor to ground.

VUNREGulated is coupled through a series voltage divider including a resistor 402 and a resistor 404 to ground. The common terminal of resistors 402, 404 is coupled directly to the analog BATTery voltage input terminal X4 of multiplexer 332. +5VA is coupled to the VDD input terminal of a temperature sensor 406. The VOUT terminal of sensor 406 is coupled directly to the analog VTEMP voltage input terminal, X6, of multiplexer 332 and through a pull-up resistor to +5VA.

The heater control circuit 322 includes two series resistors 410, 412 coupled between the HeaTeR ON/OFF terminal of µC 284 and ground. The common terminal of resistors 410, 412 is coupled to the base of a transistor 414, the collector of which is coupled through two series resistors 416, 418 to +5VA, and the emitter of which is coupled to ground. The common terminal of resistors 416, 418 is coupled to the base of a transistor 420, the emitter of which is coupled to +5VA, and the collector of which is coupled through a series resistor 422 and capacitor 424 to ground. The common terminal of resistor 422 and capacitor 424 is coupled to the −input terminal of an operational amplifier 426.

+5VA is coupled through a series resistor, a potentiometer 428 and a resistor to ground. The movable contact of potentiometer 428 is coupled to the −input terminal of operational amplifier 426. The potentiometer enables the heater plate 192 to achieve about 39° C. +5VA is coupled through a series resistor 430 and capacitor 432 to ground. The common terminal of resistor 430 and capacitor 432 is coupled to the THermistor + terminal, 196-3, of connector 196, and to the +input terminal of operational amplifier 426. The +input terminal of operational amplifier 426 is coupled through the series combination of a diode and a resistor to ground. The junction of the resistor and diode is coupled to the base of a transistor 434, the emitter of which is coupled to ground. The output terminal of operational amplifier 426 is coupled through a resistor to its −input terminal and through the series combination of a diode and a resistor to the collector of transistor 434.

The SETPoinT 2 terminal, OutPut terminal 20, of ASIC 290, is coupled through series resistors 436, 438 to +5VA. The ASIC 290 provides control of the heater plate 192 temperature at two different setpoints, 39° C. and 44° C. The second setpoint is set high to permit the heater plate 192 to attain 44° C. temperature, thereby permitting more rapid warming of samples to 39° C. The common terminal of resistors 436, 438 is coupled to the base of a transistor 440, the emitter of which is coupled to +5VA and the collector of which is coupled through a resistor to the −input terminal of operational amplifier 426. A series resistive voltage divider including a resistor 442 and a resistor 444 is coupled between the output terminal of operational amplifier 426 and ground. The common terminal of resistors 442, 444 is coupled to an analog input terminal X3 of multiplexer 332. Heater control circuit 322 operating status is thus multiplexed into μC 284. Additionally, heater control status, as reflected by the voltage at the collector of transistor 434, controls the flow of current through the heater foil 182. This is accomplished through a transistor 446, the base of which is coupled to the collector of transistor 434 and the collector of which is coupled to the − HEATER terminal, 196-2, of connector 196. The + HEATER terminal, 196-1, of connector 196 is coupled to + VUNREGulated. The emitter of transistor 446 is coupled through a parallel resistance network to ground. The base of transistor 446 is also coupled through two series diodes to ground, which limits the current through the heater foil to approximately 0.4 A. The − THermistor terminal, 196-4, of connector 196 is coupled to ground.

Terminal P1.6 of μC 284 is coupled through a diode to the −input terminal of an operational amplifier 450 in the sample port circuit 326. The +input terminal of operational amplifier 450 is coupled to VREF. The output terminal of operational amplifier 450 is coupled to the base of a transistor 452, the emitter of which is coupled through a feedback resistor to the −input terminal of operational amplifier 450 and to ground through resistance, which limits the current through the sample port LED at a constant current. The collector of transistor 452 is coupled to terminal 168-1 of the sample port connector 168. +5VA is coupled to terminal 168-2, the VDD terminal, of connector 168. VUNREGulated is coupled to terminal 168-5 of connector 168. The SAMPle IN terminal, 168-4, of connector 168 is coupled to ground through a resistor and through a capacitor to the −input terminal of an operational amplifier 456. The +input terminal of operational amplifier 456 is coupled to ground. The output terminal of operational amplifier 456 is coupled through a parallel RC feedback circuit to its −input terminal. The output terminal of operational amplifier 456 is coupled through a capacitor to the + input terminal of an operational amplifier 458. The + input terminal of operational amplifier 458 is coupled to ground through a resistor. The −input terminal of operational amplifier 458 is coupled to ground through a resistor. The output terminal of operational amplifier 458 is coupled to the cathode of a diode, the anode of which is coupled through a resistor to the −input terminal of operational amplifier 458. The output terminal of operational amplifier 458 is also coupled to the anode of a diode 460, the cathode of which is coupled through a resistor 462 to the −input terminal of operational amplifier 458. This provides a hysteresis-type configuration which has different gains depending upon whether the voltage at the +input terminal of operational amplifier 458 is greater than or less than the voltage at the −input terminal thereof. The common terminal of diode 460 and resistor 462 is coupled through the series combination of a resistor 464 and a capacitor 466 to ground. The common terminal of resistor 464 and capacitor 466 is coupled to the SAMPle DETect input terminal, X7, of multiplexer 332.

Terminal P1.7 of μC 284 is coupled through two series resistors in the magnet control circuit 328 to ground. The common terminal of these resistors is coupled to the base of a transistor 470, the emitter of which is coupled to ground. The collector of transistor 470 is coupled through series resistors to +5VA. The common terminal of these resistors is coupled to the base of a transistor 471, the emitter of which is coupled to +5VA and the collector of which is coupled to the −input terminal of an operational amplifier 472. The series combination of a resistor 474 and a resistor 476 is coupled between VREF and ground. A capacitor is coupled across resistor 476. The common terminal of resistors 474 and 476 is coupled to the +input terminal of operational amplifier 472.

The output terminal of operational amplifier 472 is coupled to the base of a magnet coil 144-driver transistor 478. The emitter of transistor 478 is coupled through a resistor to ground, which limits the current through the magnet coil at a constant current, and through a feedback resistor to the −input terminal of operational amplifier 472. A capacitor is coupled between the −input terminal of operational amplifier 472 and ground. The collector of transistor 478 is coupled to terminal 156-3 of connector 156. Terminal 156-1 of connector 156 is coupled to VUNREGulated. Coil 144 is coupled across connectors 156-1 and 156-3. The series combination of a resistor and a capacitor is also coupled across connectors 156-1 and 156-3. A flyback diode is also coupled across terminals 156-1 and 156-3.

The bar code LED driver circuit 330 which is associated with photodiode 224 includes eight bar code-illuminating LEDs 484-1–484-8. The anode of LED 484-1 is coupled to +5V and its cathode is coupled to the Anode terminal of optical switch 486. Optical switch 486 provides the source and detector for flag 264 to indicate when the strip adapter top and bottom assemblies 130, 132 are closed together. The collector terminal, C, of optical switch 486 is coupled to InPut terminal 3 of ASIC 290, and through a load resistor to +5V. The cathode terminal, K, of optical switch 486 is coupled through a load resistor to the collector of a transistor 490-1, the emitter of which is coupled to ground and the base of which is coupled through a resistor to OutPut terminal 17 of ASIC 290. The anodes of the remaining LEDs 484-2–484-8 are coupled through a common load resistance to +5V. The cathodes of LEDs 484-2–484-8 are coupled to the collectors of transistors 490-2–490-8, respectively. The emitters of transistor 490-2–490-8 are coupled to ground. The bases of transistor 490-2–490-8 are coupled through respective resistors to OutPut terminals 16-10, respectively, of ASIC 290.

LEDs 484-1–484-8 are mounted on PCB 114 and emit light through respective slit openings 204-1–204-8, respectively. LED's 484-1–484-8 are sequentially energized through transistors 490-1–490-8, respectively. The presence or absence of a bar code in region 492 of a particular test strip 101 placed in instrument 100 is sensed by transmission of light from a respective LED 484-1–484-8 by conduction of photodiode 224. This identifies certain test strip 101 lot-specific parameters for instrument 100.

In operation, a sample 514 is deposited in the test strip 101 sample well 494 over location 210. Radiation from LED 164, which is strobed at 0.25 sec. intervals, detected by photodiode 166 establishes the dosing of strip 101. START LED 238 is strobed at 50 msec. intervals until the arrival of the sample 514 at the region of strip 101 over START LED 238 is established by the radiation from START LED 238 detected by photodiode 242. The flow time of the sample 514 between the sample application point at well 494 and the detection of the arrival of the sample 514 over the START LED 238 establishes the sample 514 as blood or a control. The control solutions, being less viscous, flow between these two locations more rapidly, and this is detected by the instrument 100. The minimum flow time that the instrument 100 will interpret as blood and/or the maximum flow time that the instrument 100 will interpret as control can be varied from strip lot to strip lot by changing (a) parameter(s) in the user-insertable EEPROM key 119. This relieves the user from the need to indicate to the instrument 100 or otherwise record when a quality control check is being conducted.

After photodiode 242 has detected the arrival of the sample 514 over the START LED 238, the START LED 238 is deenergized and the FILL LED 240 is energized. The next decrease in radiation detected by photodiode 242 indicates the arrival of the sample 514 over the FILL region of the strip 101. The elapsed time between detection by photodiode 242 of arrival of the sample 514 over START LED 238 and detection by photodiode 242 of arrival of the sample 514 over FILL LED 240 is used by the instrument 100 to determine whether the volume of the sample 514 which was applied is adequate to conduct a coagulation test. If the instrument 100 determines that the applied sample 514 volume was inadequate to conduct a test, the instrument 100 provides an error message and returns to its ready state. If the instrument 100 determines that the applied sample 514 volume was sufficient to conduct a coagulation time test reliably, FILL LED 240 is deenergized and MAIN assay LED 244 is energized. Electromagnet 140 is also energized and monitoring by photodiode 242 of MAIN assay LED 244 radiation begins. Magnet assembly 140, when driven by magnet current control circuit 328, stirs ferromagnetic particles from the test strip 101 borne by the sample 514, be it blood or control. The particles reorient themselves along the combined lines of force of magnet assembly 140 and bias magnet 154 and provide a modulated light transmission profile of the sample. This transmission profile, illustrated in FIG. 16 at 500, is detected by photodiode 242 and is multiplexed (DETect-AC1-DC) via multiplexer 332 and A/D 324 into µC 284. Coagulation of the sample causes the reduction in the modulation in this transmission profile as described in U.S. Pat. Nos. 4,849,340 and 5,110,727. Waveform 500 is rectified and the envelope 502 of the rectified waveform 500 is formed.

To reduce the likelihood of double dosing the strip 101, the ratio of START to FILL time-to-sample application to START time is formed. This ratio is compared to a parameter provided from key 119. The ratio must be less than the parameter. Otherwise the instrument 100 will conclude that the strip 101 has been double dosed and will generate an error message. Double dosing is to be avoided because it can refluidize the ferromagnetic particles, producing an erroneous coagulation time reading.

FIGS. 17a–b are much-enlarged fragmentary longitudinal sectional views of a strip 101 taken along section lines 17—17 of FIG. 4. Generally, in the absence of liquid blood, a blood fraction or control (FIG. 17a), the indices of refraction of the strip bottom 506 and top 508 and the air-filled sample volume 510 between them are such that the level of light from LED 164 returning to photodiode 166 is relatively higher. This is illustrated at region 512 of FIG. 18. A liquid sample 514, be it blood, a blood fraction or a control, is deposited into the sample well 494 of strip 101 and migrates into region 510 of strip 101 over region 211 of instrument 100. Owing generally to the matching of the strip bottom 506's, top 508's and liquid 514's indices of refraction and absorption in the case of clear liquids, and generally to absorption and scattering effects in the case of whole blood, a relatively lower light level is detected by photodiode 166 as illustrated at region 522 in FIG. 18 when a liquid is present on strip 101 adjacent region 211. This optical detection scheme permits a clear control to be used.

FIG. 19 illustrates two waveforms useful in understanding the start noise immunization technique employed in an instrument according to the present invention. It has been experimentally determined that, unless provisions are made in instrument 100 to prevent it, instrument 100 can be falsely triggered by negative-going noise spikes 526 that are generated during application of a sample to a test strip 101. Such spikes 526 are caused when the user accidentally taps or moves the strip 101 from side to side or in and out of the optics assembly 116 during sample application. Such negative-going spikes 526 can be greater than the instrument 100's −60 mV starting threshold, but are typically shorter in duration than the negative-going start signal 528 and are preceded or followed immediately by positive-going spikes 530. This is in contrast to the actual liquid sample signal 528 which is only negative-going. This difference is used to discriminate effectively between signal 528 and noise 526, 530. The instrument 100's START algorithm discriminates between short (noise) 526, 530 and long (start signal) 528 duration signals using negative trend, rate of signal change and negative threshold criteria. The flow of the START algorithm includes the following illustrative characteristics: three consecutive data points sampled 50 msec apart must be negative relative to a reference and have rates of signal change more negative than −7.3 mV/50 msec (−30 counts of the A/D converted input signal at 0.243 mV/count) with an absolute signal change more negative than the −60 mV (−246 counts) instrument 100 start threshold. The parameters stored in the EEPROM 119 then would include a signal delta of −30 counts and a start threshold of −246 counts.

What is claimed is:

1. An instrument for determining a characteristic of a biological fluid or a control, the instrument comprising a radiation-reflective surface, a first source for irradiating the surface, a first detector for detecting radiation reflected from the surface, and means for determining the characteristic based on the detected radiation, and a slide for holding a sample of the biological fluid or control, the characteristic of which is to be determined, the slide having two opposed walls transparent to the radiation, the first source and first detector being adjacent a first one of said two opposed walls and the radiation-reflective surface being disposed adjacent a second of said two opposed walls, a system for supplying power and regulating supplied power from one of multiple power sources to the instrument, the system comprising first and second power sources, first coupling means for selectively coupling the system to the first power source, second coupling means for selectively coupling the system to the second power source, at least one capacitor coupled to the first and second coupling means for storing energy supplied by the first and second power sources, and means for comparing a voltage supplied by the first power source to a voltage supplied by the second power source, and for controlling the first coupling means to decouple the system from the first power source when the voltage supplied by the second power source exceeds the voltage supplied by the first power source.

2. The instrument of claim 1 wherein the characteristic of a biological fluid or a control comprises a clotting characteristic of blood, a blood fraction or a control.

3. The instrument of claim 1 wherein the first power source comprises a battery provided in the instrument and the second power source comprises an AC-to-DC converter for supplying a voltage having a higher magnitude than the battery's voltage when the converter is coupled to a line voltage source.

4. The instrument of claim 1 further comprising an ON/OFF switch for energizing the instrument, third coupling means for selectively coupling one of the first and second coupling means to the instrument, means for coupling the third coupling means to the ON/OFF switch, and means for coupling the third coupling means to the first and second coupling means.

5. The instrument of claim 1, 3 or 4 and further comprising a controller for orderly de-energizing the instrument, the at least one capacitor for storing sufficient energy to permit the controller to orderly de-energize the instrument in the absence of power from the first or second power sources, means for monitoring the voltage supplied to the instrument by one of the first and second power sources and for signaling the controller to orderly de-energize the instrument if the monitored voltage does not exceed a threshold, fourth means for coupling the controller to the at least one capacitor storing, sufficient energy to permit the controller to orderly de-energize the instrument, fifth means for coupling the means for monitoring the voltage supplied to the instrument by one of the first and second power sources to the first and second coupling means, and sixth means for coupling the means for monitoring the voltage supplied to the instrument by one of the first and second power sources to the controller.

6. A method for supplying power and regulating supplied power to an instrument for determining a characteristic of a biological fluid or control, the instrument comprising a radiation-reflective surface, a first source for irradiating the surface, a first detector for detecting radiation reflected from the surface, the method comprising providing first and second power sources, providing at least one capacitor, coupling the at least one capacitor to the first and second power sources, comparing a voltage supplied to at least one of the first source and first detector by the first power source to a voltage supplied to at least one of the first source and first detector by the second power source, providing means selectively coupling the at least one of the first source and first detector selectively to the first power source, and decoupling the at least one of the first source and first detector from the first power source when the voltage supplied to the at least one of the first source and first detector by the second power source exceeds the voltage supplied to the at least one of the first source and first detector by the first power source.

7. The method of claim 6 wherein determining a characteristic of a biological fluid or a control comprises determining a clotting characteristic of blood, a blood fraction or a control.

8. The method of claim 6 wherein the step of providing first and second power sources to the at least one of the first source and first detector comprises providing a battery and providing an AC-to-DC converter for supplying to the at least one of the first source and first detector a voltage having a higher magnitude than the magnitude of the battery's voltage when the converter is coupled to a line voltage source.

9. The method of claim 6 and further comprising providing an ON/OFF switch for energizing the at least one of the first source and first detector, and coupling one of the first and second power sources by the ON/OFF switch to the at least one of the first source and first detector.

10. The method of claim 6, 8 or 9 wherein the step of providing at least one capacitor comprises providing at least one capacitor for storing sufficient energy to permit orderly de-energizing of the at least one of the first source and first detector, monitoring the voltage supplied to the at least one of the first source and first detector by one of the first and second power sources, signalling a controller to orderly de-energize the at least one of the first source and first detector if the monitored voltage does not exceed a threshold, and orderly de-energizing the at least one of the first source and first detector.

11. An instrument for determining a characteristic of a biological fluid or a control contained in a slide having first and second opposed walls transparent to radiation, the instrument comprising a radiation-reflective surface disposed adjacent the first wall, , a radiation source disposed adjacent the second wall, a radiation detector disposed adjacent the second wall, a processor coupled to the radiation source and detector for determining the characteristic based on the detected radiation, a first power source selectively coupled to the radiation source and detector, a second power source selectively coupled to the radiation source and detector, at least one capacitor coupled to the first and second power sources for storing energy supplied by the first and second power sources, and a voltage comparator circuit that compares a first voltage supplied by the first power source to a second voltage supplied by the second power source, and decouples the radiation source and detector the first power source when the second voltage exceeds the first voltage.

12. The instrument of claim 11 wherein the characteristic of a biological fluid or a control comprises a clotting characteristic of blood, a blood fraction or a control.

13. The instrument of claim 11 wherein the first power source comprises a battery provided in the instrument and the second power source comprises an AC-to-DC converter for supplying a second voltage having a higher magnitude than the battery's voltage when the converter is coupled to a line voltage source.

14. The instrument of claim 11 further comprising an ON/OFF switch for energizing the instrument and a circuit that selectively couples the ON/OFF switch to one of the first and second power sources to the instrument.

15. The instrument of claim 11, 13 or 14 and further comprising a controller for orderly de-energizing the instrument, the at least one capacitor stores sufficient energy to permit the controller to orderly de-energize the instrument in the absence of power from the first or second power sources, and a voltage monitor circuit coupled to the controller and first and second power sources that monitors the voltage supplied to the instrument by one of the first and second power sources and signals the controller to orderly de-energize the instrument if the monitored voltage does not exceed a threshold.

* * * * *